(12) United States Patent
Wang et al.

(10) Patent No.: US 11,420,947 B2
(45) Date of Patent: Aug. 23, 2022

(54) (S)-N-HYDROXY-2-(2-(4-METHOXYPHENYL) BUTANAMIDO)THIAZOLE-5-CARBOXAMIDE AND PHARMACEUTICALLY ACCEPTABLE SALTS THEREOF

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translational Drug Development, LLC, Scottsdale, AZ (US)

( * ) Notice: Subject to any disclaimer, the term of this patent is extended or adjusted under 35 U.S.C. 154(b) by 0 days.

(21) Appl. No.: 17/344,680

(22) Filed: Jun. 10, 2021

(65) Prior Publication Data

US 2021/0347747 A1   Nov. 11, 2021

Related U.S. Application Data

(63) Continuation of application No. PCT/US2019/065299, filed on Dec. 9, 2019.

(60) Provisional application No. 62/777,600, filed on Dec. 10, 2018.

(51) Int. Cl.
| | | |
|---|---|---|
| *A61K 45/06* | (2006.01) | |
| *A61P 35/04* | (2006.01) | |
| *C07D 277/593* | (2006.01) | |

(52) U.S. Cl.
CPC .......... *C07D 277/593* (2013.01); *A61K 45/06* (2013.01); *A61P 35/04* (2018.01)

(58) Field of Classification Search
CPC ...... C07D 277/593; A61P 35/04; A61K 45/06
See application file for complete search history.

(56) References Cited

U.S. PATENT DOCUMENTS

| | | | |
|---|---|---|---|
| 9,221,773 B2 * | 12/2015 | Wang | .................. C07D 277/56 |
| 2008/0269182 A1 | 10/2008 | Pluda et al. | |
| 2013/0045982 A1 * | 2/2013 | Wang | ...................... A61P 35/00 |
| | | | 514/256 |
| 2014/0228416 A1 | 8/2014 | Blackburn et al. | |
| 2017/0333404 A1 | 11/2017 | Miller et al. | |

FOREIGN PATENT DOCUMENTS

CN          103012280 A        4/2013

OTHER PUBLICATIONS

Luqman, "Recent Advances in Plasticizers," 2012. (Year: 2012).*
Lee, Ju-Hee et al., "Creation of a histone deacetylase 6 inhibitor and its biological effects", PNAS, 112 (39): 12005-12010 (2015).
McCullagh, James V., "Enantiomeric Separation/Resolution: Analyzing the Experimental Results of the Resolution of the S- and R-stereoisomers of (+/−) ibuprofen, (2-(4'-isobutylphenyl)-propionic acid", pp. 1-6, Retrieved from the Internet: <URL:https://web.archive.org/web/2018045194839/http://www.chemconnections.org/organic/chem226/Labs/opt-rotation/ibupro-resolution-09.html> (Apr. 5, 2018).
Oh, Bo Ram et al., "Therapeutic effect of a novel histone deacetylase 6 inhibitor, CKD-L, on collagen-induced arthritis in vivo and regulatory T cells in rheumatoid arthritis in vitro", Arthritis Research & Therapy, 19:1-16 (2017).
International Search Report for PCT/US2019/065299 dated Feb. 7, 2020 (5 pages).
Written Opinion of the International Searching Authority for PCT/US2019/065299 dated Feb. 7, 2020 (11 pages).

* cited by examiner

*Primary Examiner* — Jared Barsky
(74) *Attorney, Agent, or Firm* — Rodney J. Fuller; Booth Udall Fuller, PLC

(57) ABSTRACT

The invention relates to the compound (S)-n-hydroxy-2-(2-(4-methoxyphenyl) butanamido)thiazole-5-carboxamide, which is a novel histone deacetylase inhibitor. The invention further relates to the use of the compound for the inhibition of histone deacetylating activities of HDAC isoforms and treatment of histone deacetylase (HDAC)-associated diseases. The invention also relates to the pharmaceutical compositions and the making of the pharmaceutical compositions comprising the compound.

8 Claims, 7 Drawing Sheets

(S)-N-HYDROXY-2-(2-(4-METHOXYPHENYL) BUTANAMIDO)THIAZOLE-5-CARBOXAMIDE AND PHARMACEUTICALLY ACCEPTABLE SALTS THEREOF

CROSS-REFERENCE TO RELATED APPLICATIONS

This application is a continuation of International Patent Application No. PCT/US2019/065299, filed on Dec. 9, 2019, which claims the benefit of and priority to U.S. Provisional Patent Application No. 62/777,600, filed on Dec. 10, 2018, the contents of each of which are incorporated herein by reference in their entireties.

TECHNICAL FIELD

The invention relates to thiazole compounds, pharmaceutical compositions, and use of the compounds and pharmaceutical compositions to inhibit histone deacetylase (HDAC) and treat HDAC-associated diseases.

BACKGROUND OF THE INVENTION

Cancer is the second leading cause of death in the United States. Despite breakthroughs that have led to decreased mortality, many cancers remain refractory to treatment. Also, many cancers often develop resistance to current chemotherapies over time. The typical treatments such as chemotherapy, radiotherapy, and surgery also cause a broad spectrum of undesirable side effects.

Histone deacetylases (HDACs) are a family of enzymes that deacetylate histones and non-histone proteins known to modulate gene transcription. HDACs have been associated with the proliferation and differentiation of various cell types as well as pathogenesis of diseases including cancer, interstitial fibrosis, autoimmune and inflammatory diseases, and metabolic disorders. There is a need for novel HDAC inhibitors and methods of treating cancer and other histone deacetylase-associated diseases using such novel HDAC inhibitors, either alone or in combination with other therapeutic modalities.

Chiral resolution of a racemic mixture of a novel HDAC inhibitor may increase the inhibitor's ability to inhibit HDAC, improve the pharmacokinetics of the inhibitor, or both. However, chiral chromatography to obtain optically pure enantiomers is associated with uncertainties such as low yield, and certain enantiomer being unstable in certain solvent systems. Type of chiral column, the combination of solvent system, and gradient, etc. are key variables during method development. There is a need for overcoming technical challenges and resolving racemates of novel HDAC inhibitors.

SUMMARY OF THE INVENTION

In certain aspects, the present invention provides (S)—N-hydroxy-2-(2-(4-methoxyphenyl)butanamido)thiazole-5-carboxamide

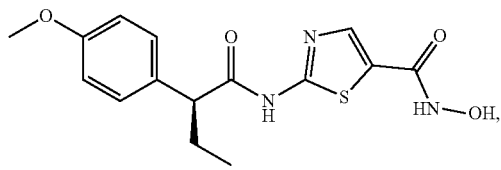 [SMILES: CC[C@H](C(=O)Nc1ncc(C(=O)NO)s1)c1ccc(OC)cc1]

or a pharmaceutically acceptable salt, ester, derivative, analog, prodrug, or solvate thereof.

The present invention also provides a pharmaceutical composition for treating a histone deacetylase (HDAC)-associated disease, comprising: an active ingredient, wherein the active ingredient comprises at least a first active ingredient selected from the group consisting of: (S)—N-hydroxy-2-(2-(4-methoxyphenyl) butanamido)thiazole-5-carboxamide, N-hydroxy-2-(2-(4-methoxyphenyl) butanamido)thiazole-5-carboxamide, and a pharmaceutically acceptable salt, ester, derivative, analog, prodrug, or solvate thereof; and a pharmaceutically acceptable carrier.

In other aspects, the present invention provides a method of fabricating a pharmaceutical composition for treating a histone deacetylase (HDAC)-associated disease, comprising mixing an active ingredient with a pharmaceutically acceptable carrier in a thermokinetic mixer at less than about 250° C. for less than 300 seconds, wherein the active ingredient comprises at least a first active ingredient selected from the group consisting of: (S)—N-hydroxy-2-(2-(4-methoxyphenyl) butanamido)thiazole-5-carboxamide, N-hydroxy-2-(2-(4-methoxyphenyl)butanamido)thiazole-5-carboxamide, and pharmaceutically acceptable salt, ester, derivative, analog, prodrug, or solvate thereof.

In one aspect, the (S)—N-hydroxy-2-(2-(4-methoxyphenyl)butanamido)thiazole-5-carboxamide, or pharmaceutically acceptable salt, ester, derivative, analog, prodrug, or solvate thereof, is 80-100% of the first active ingredient, by weight.

In certain aspects, the active ingredient further comprises a second active ingredient.

In one aspect, the second active ingredient comprises a DNA methyltransferase inhibitor, a bromodomain inhibitor, or both.

In certain implementations, the amount of the first active ingredient, the second active ingredient, or both, is a therapeutically effective amount.

In other implementations, the pharmaceutically acceptable carrier is selected from the group consisting of: a pharmaceutical polymer carrier, a processing agent, a surfactant, and combinations thereof. Non-limiting examples of the pharmaceutical polymer carrier include a cellulosic pharmaceutical polymer, a cross-linked pharmaceutical polymer, a high melt viscosity pharmaceutical polymer, a non-ionic pharmaceutical polymer, a non-ionic, cellulosic pharmaceutical polymer, a non-ionic, water-soluble pharmaceutical polymer, a thermally labile pharmaceutical polymer, a water-soluble pharmaceutical polymer, a water-soluble, cellulosic pharmaceutical polymer, and combinations thereof.

In yet other aspects, the pharmaceutical polymer carrier is selected from the group consisting of: carbomer, cellulose acetate butyrate, cellulose acetate phthalate, cellulose acetate trimelletate, crospovidone, croscarmellose sodium, dimethylaminoethyl methacrylate-methacrylic acid ester copolymer, ethylacrylate-methylmethacrylate copolymer, ethylcellulose, hydroxyethylcellulose, hydroxypropylcellulose, hydroxypropyl methylcellulose, hydroxypropylmethylcellulose acetate succinate, hydroxypropylmethylcellulose phthalate, poly(butyl methacylate-co-(2-dimethylaminoethyl) methacrylate-co-methyl methacrylate) 1:2:1, polycarbophil, poly(ethylene glycol), poly(ethylene oxide), poly (methacrylate ethylacrylate) (1:1) copolymer, poly (methacrylate methylmethacrylate) (1:1) copolymer, poly (methacrylate methylmethacrylate) (1:2) copolymer, poly (vinyl acetate)-co-poly(vinylpyrrolidone) copolymer, poly (vinyl acetate) phthalate, poly(vinyl alcohol), polyvinyl caprolactam-polyvinyl acetate-polyethylene glycol graft copolymer, poly(vinylpyrrolidone), sodium carboxymethylcellulose, and combinations thereof.

In one aspect, the processing agent comprises a plasticizer. In another aspect, the surfactant is selected from the group consisting of: dioctyl sodium sulphosuccinate, glycerol polyethylene glycol oxystearate-fatty acid glycerol polyglycol esters-polyethylene glycols-glycerol ethoxylate, glycerolpolyethylene glycol ricinoleate-fatty acid esters of polyethylene glycol-polyethylene glycols-ethoxylated glycerol, polyoxyethylene (20) sorbitan monooleate, sodium dodecyl sulfate, sorbitan laurate, vitamin E TPGS, and combinations thereof.

In some implementations, the present invention provides a method of inhibiting the histone deacetylating activity of a histone deacetylase (HDAC) isoform in a cell, comprising: contacting the cell with a composition comprising a compound selected from the group consisting of: (S)—N-hydroxy-2-(2-(4-methoxypheny 1)butanamido)thiazole-5-carboxamide, N-hydroxy-2-(2-(4-methoxyphenyl)butanamido) thiazole-5-carboxamide, and a pharmaceutically acceptable salt, ester, derivative, analog, prodrug, or solvate thereof.

In certain aspects, the composition inhibits the histone deacetylating activity of the HDAC isoform with a half maximal inhibitory concentration ($IC_{50}$) of 0.0005-2 µM.

In some implementations, the HDAC isoform is selected from the group consisting of: HDAC1, HDAC2, HDAC3, HDAC6, and HDAC10. In other implementations, the HDAC isoform is selected from the group consisting of: HDAC1, HDAC3, HDAC6, and HDAC10.

In one aspect, the composition inhibits the histone deacetylating activity of the HDAC isoform by at least 30%. In another aspect, the cell is selected from the group consisting of: a cancer cell, a neuronal cell, a cell of the immune system, a cell of the circulatory system, and combinations thereof. In yet other aspects, the cancer cell is selected from the group consisting of: an acute lymphocytic leukemia (ALL) cell, an acute myeloid leukemia (AML) cell, an acute promyelocytic leukemia (APL) cell, adenosquamous carcinoma of the pancreas, a blood cancer cell, a brain tumor cell, a breast cancer cell, a cervical squamous cell, a chronic myeloid leukemia (CML) cell, a colon cancer cell, a diffuse large B-cell lymphoma (DLBCL) cell, an endometrial cancer cell, a gastrointestinal stromal tumor (GIST) cell, a glioblastoma (GBM) cell, a hepatocellular carcinoma cell, a Hodgkin lymphoma cell, a leukemia cell, a liver cancer cell, a lung cancer cell, a melanoma cell, a mesothelioma cell, a multiple myeloma cell, a non-Hodgkin's lymphoma cell, a non-small cell lung cancer (NSCLC) cell, a neuroblastoma cell, an ovarian cancer cell, a pancreatic cancer cell, a pancreatic ductal adenocarcinoma cell, a peripheral T-cell lymphoma cell, a pharynx cancer cell, a prostate cancer cell, a renal cancer cell, a rhabdomyocarcoma cell, a skin cancer cell, a thyroid cancer cell, a tongue tumor cell, a uterine cancer cell, a Waldenstrom myeloma cell, and combinations thereof.

In one aspect, the cancer is selected from the group consisting of: adenosquamous carcinoma of the pancreas, diffuse-type gastric cancer associated with RHOA mutation, malignant rhabdoid tumor, ovarian small cell carcinoma of hypercalcemic type, uveal melanoma, and combinations thereof.

In certain implementations, the composition inhibits cell proliferation, induces cell death, or both.

In other implementations, the present invention provides a method of treating a histone deacetylase (HDAC)-associated disease in a subject, comprising administering to the subject a composition, wherein the composition comprises at least a first active ingredient selected from the group consisting of: (S)—N-hydroxy-2-(2-(4-methoxyphenyl)butanamido)thiazole-5-carboxamide, N-hydroxy-2-(2-(4-methoxyphenyl)butanamido)thiazole-5-carboxamide, and a pharmaceutically acceptable salt, ester, derivative, analog, prodrug, or solvate thereof.

In some aspects, the disease is selected from the group consisting of: cancer, an autoimmune disorder, an inflammatory disorder, a neurodegenerative disease, and combinations thereof. In other aspects, the cancer is selected from the group consisting of: acute lymphocytic leukemia (ALL), acute myeloid leukemia (AML), acute promyelocytic leukemia (APL), breast cancer, chronic myeloid leukemia (CML), colon cancer, diffuse large B-cell lymphoma (DLBCL), gastrointestinal stromal tumor (GIST), glioblastoma (GBM), hepatocellular carcinoma, Hodgkin's lymphoma, leukemia, lung cancer, multiple myeloma, non-Hodgkin's lymphoma, non-small cell lung cancer (NSCLC), neuroblastoma, ovarian cancer, pancreatic ductal adenocarcinoma, peripheral T-cell lymphoma, prostate cancer, uterine cancer, Waldenstrom myeloma, and combinations thereof.

In yet other aspects, the autoimmune or inflammatory disorder is selected from the group consisting of: airway hyperresponsiveness, Crohn's disease, inflammatory bowel disease, multiple sclerosis, psoriasis, rheumatoid arthritis, systemic lupus erythematosus, type 1 diabetes, ulcerative colitis, and combinations thereof.

In one aspect, the neurodegenerative disorder is selected from the group consisting of: Alzheimer's disease (AD), amyotrophic lateral sclerosis (ALS), cerebral ischemia, Huntington's disease (HD), Parkinson's disease (PD), spinal muscular atrophy, and combinations thereof.

In certain implementations, the composition is administered at 10-400 mg per kg of the subject about every 4, 8, 12, 16, or 24 hours. In other implementations, the composition is administered at 10-350 mg per kg of the subject, 10-300 mg per kg of the subject, 10-250 mg per kg of the subject, 10-200 mg per kg of the subject, 10-150 mg per kg of the subject, or 10-100 mg per kg of the subject. In yet other implementations, the composition is administered once every 1 hour, every 2 hours, every 3 hours, every 4 hours, every 6 hours, every 8 hours, every 10 hours, every 12 hours, every 14 hours, every 16 hours, every 18 hours, every 20 hours, every 22 hours, or every 24 hours.

In some aspects, the subject is a human. In other aspects, the composition further comprises a second active ingredient. In certain aspects, the second active ingredient is a therapeutic agent selected from the group consisting of: a chemotherapy drug, a MEK inhibitor, an agent that enhances antigen presentation, an agent that enhances an effector cell response, an agent decreases tumor immunosuppression, and combinations thereof.

In one aspect, the chemotherapy drug is selected from the group consisting of: pomalidomide, dexamethasone, and combinations thereof. In another aspect, the agent that enhances antigen presentation is selected from the group consisting of: an agent that enhances lysis of tumor cells, an agent that stimulates a phagocyte, an agent that disinhibits a phagocyte, an agent that activates a dendritic cell, an agent that activates a macrophage, an agent that recruits a dendritic cell, an agent that recruits a macrophage, a vaccine, and combinations thereof.

In certain implementations, the agent that enhances antigen presentation is selected from the group consisting of: a cell-based vaccine, an antigen-based vaccine, an oncolytic virus, a Type I interferon (IFN) activator, a bi-specific cell engager, a tri-specific cell engager, and combinations thereof.

In other implementations, the agent that enhances antigen presentation is selected from the group consisting of: an agonist of Stimulator of Interferon Genes (a STING agonist), an agonist of a Toll-like receptor (TLR), a TIM-3 modulator, a vascular endothelial growth factor receptor (VEGFR) inhibitor, a c-Met inhibitor, a TGFb inhibitor, an IDO/TDO inhibitor, an A2AR antagonist, an oncolytic virus, a vaccine, a bi-specific cell engager, a tri-specific cell engager, a bi-specific antibody molecule, a tri-specific antibody molecule, an IDO/TDO inhibitor, and combinations thereof.

In yet other implementations, the agent that enhances an effector cell response is selected from the group consisting of: a bi-specific cell engager, a bi-specific T cell engager, an agent that activates a tumor infiltrating lymphocyte (TIL), an agent that disinhibits a TIL, an immunomodulator, an inhibitor of inhibitor of apoptosis protein (IAP), an inhibitor of target of rapamycin (mTOR), an interleukin, an interleukin variant, a lymphocyte activator, an NK cell modulator, an NK cell therapy, a T cell modulator, a tri-specific cell engager, a vaccine, and combinations thereof.

In certain aspects, the agent that decreases tumor immuno-suppression is selected from the group consisting of: an agent that increases M2 polarization, an agent that increases T cell recruitment, an agent that increases $T_{reg}$ depletion, an agent that modulates the activity of macrophage 2, an agent that modulates the activity of MDSCs, an agent that modulates the activity of $T_{reg}$, an agent that modulates the level of macrophage 2, an agent that modulates the level of MDSCs, an agent that modulates the level of $T_{reg}$, and combinations thereof.

In one aspect, the agent that decreases tumor immuno-suppression is selected from the group consisting of: an immunomodulator, a CSF-1/1R inhibitor, an IL-17 inhibitor, an IL-1.beta. inhibitor, a CXCR2 inhibitor, an inhibitor of a phosphoinositide 3-kinase, a BAFF-R inhibitor, a MALT-1/BTK inhibitor, a JAK inhibitor, a CRTH2 inhibitor, a VEGFR inhibitor, an IL-15 or a variant thereof, a CTLA-4 inhibitor, an IDO/TDO inhibitor, an A2AR antagonist, a TGFb inhibitor, a PFKFB3 inhibitor, an inhibitor of an immune checkpoint molecule, and combinations thereof.

In another aspect, the second active ingredient is a MEK inhibitor selected from the group consisting of N—((S)-2,3-Dihydroxy-propyl)-3-(2-fluoro-4-iodo-phenylamino)-isonicotinamide, CI-1040, PD035901, AZD6244, GSK1 120212, GDC-0973, U0126, XL-518, ARRY-162, ARRY-300, PD184161, PD184352, PD0325901, ARRY-142886 (AZD6244), R04927350, PD0325901, CIP-1374, TAK-733, CH4987655, RDEA119, trametinib, cobimetinib, refametinib, selumetinib, binimetinib, PD098059, U0126, CH4987655, CH5126755, GDC623, a pharmaceutically acceptable salt thereof, and a combination thereof.

In yet other aspects, the pharmaceutically acceptable salt is selected from the group consisting of: aluminum, calcium, magnesium, potassium, sodium, zinc, and combinations thereof.

In other implementations, the present invention provides a method of synthesizing a pharmaceutical compound of formula 1a, the method comprising:

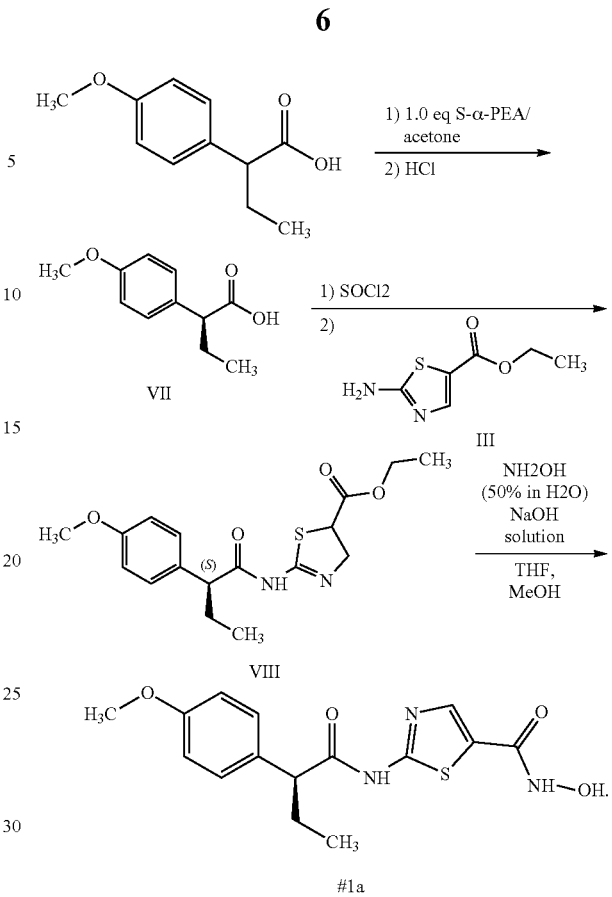

In certain aspects, the method comprises a synthetic scheme developed specifically for the starting material (i.e., 2-(4-methoxyphenyl)butanoic acid) and includes a chiral selective precipitation (i.e., crystallization) induced by a unique reagent (i.e., S-α-phenethylamine also known as S-α-PEA) in the first step. In this first step, small changes in the physical properties of the starting material such as polarity, solubility, etc. may affect the crystallization. A change or shift of functional groups in the starting material may have a significant impact on these physical properties.

BRIEF DESCRIPTION OF THE DRAWINGS

FIG. 2 illustrates preferential and significant tumor uptake and retention of #1a.

FIG. 6 depicts the crystal structure of #1a.

DETAILED DESCRIPTION OF THE INVENTION

Figure 1:
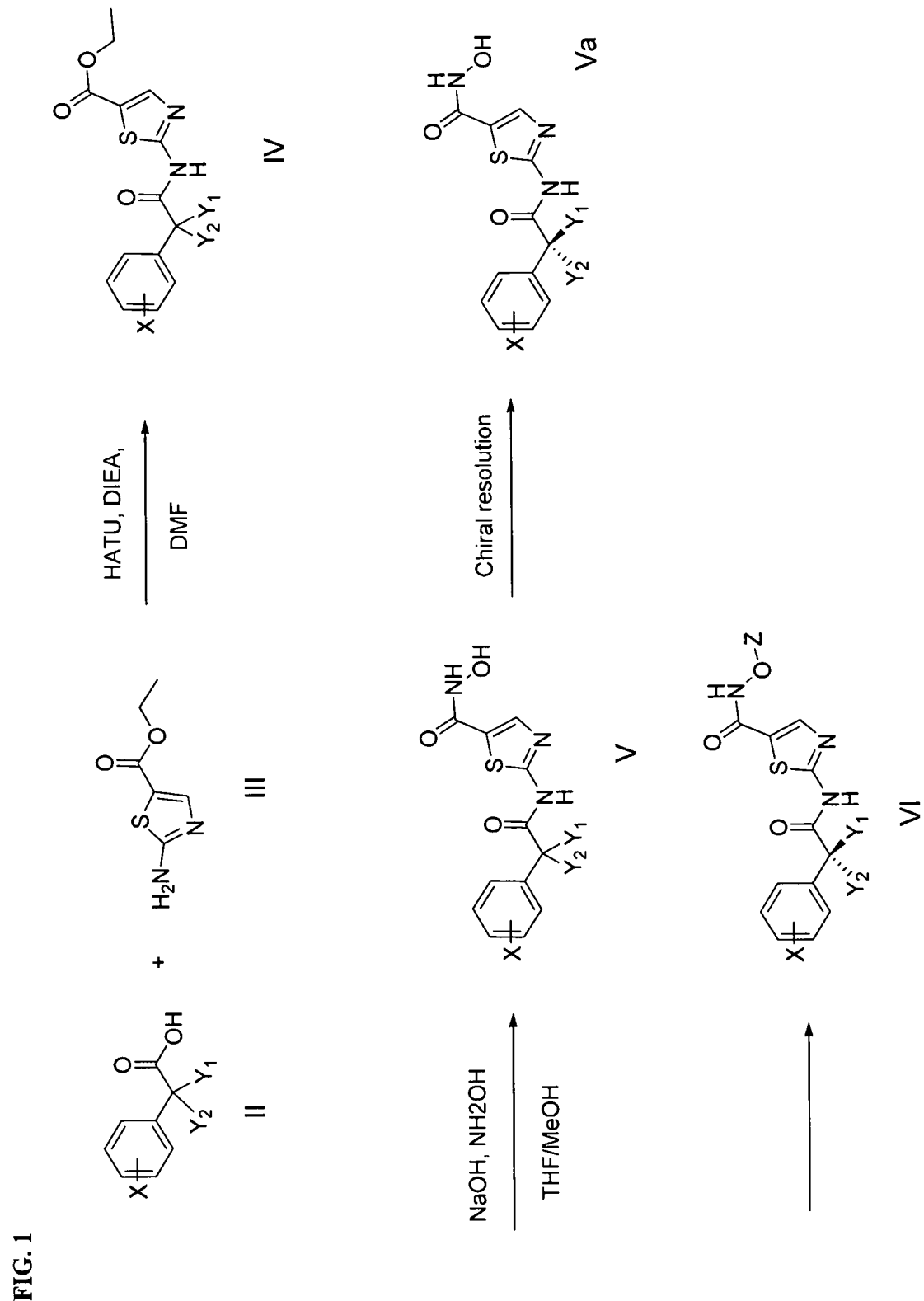
FIG. 1 depicts the general synthetic scheme of N-hydroxy-2-(2-(4-methoxyphenyl) butanamido)thiazole-5-carboxamide.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. Inventors are fully aware that they can be their own lexicographers if desired.

Inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that the noun, term, or phrase is given its broadest possible meaning.

The singular forms "a," "an," and "the" include plural referents unless the context clearly dictates otherwise. Thus, for example, reference to "an agent" includes reference to one or more of such agents.

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation, is sufficient to enable one to implement the various forms of the invention. It should be noted that there are many different and alternative configurations, devices, compositions, and technologies to which the disclosed invention may be applied. The full scope of the inventions is not limited to the examples that are described below.

The present disclosure relates to a compound (S)—N-hydroxy-2-(2-(4-methoxyphenyl) butanamido)thiazole-5-carboxamide (compound #1a, hereinafter "#1a"), its pharmaceutically acceptable salt, ester, derivative, analog, prodrug, or solvate thereof.

The disclosure encompasses any physiochemical form #1a may assume. Non-limiting examples of the physiochemical forms include hydrated forms, solvated forms, crystalline (known or yet to be disclosed), polymorphic crystalline, and amorphous form, etc. Methods of generating such physiochemical forms will be known by one skilled in the art.

The present disclosure also relates to a pharmaceutical composition for treating a histone deacetylase (HDAC)-associated disease. The pharmaceutical composition comprises at least a first active ingredient selected from the group consisting of: (S)—N-hydroxy-2-(2-(4-methoxyphenyl) butanamido)thiazole-5-carboxamide (#1a), N-hydroxy-2-(2-(4-methoxyphenyl) butanamido)thiazole-5-carboxamide (compound #1, hereinafter "#1"), and pharmaceutically acceptable salt, ester, derivative, analog, prodrug, or solvate thereof.

In some aspects, #1a, pharmaceutically acceptable salt, ester, derivative, analog, prodrug, or solvate thereof, is 80-100% of the first active ingredient, by weight, or any percent range in between, e.g., 85-100%, 85-99.99%, 90-99.99%, 90-99.9%, 92.5%-99.9%, 92.5%-99.5%, 95-99.5%, 95-99%, or 97.5-99%, etc. In other aspects, #1a, pharmaceutically acceptable salt, ester, derivative, analog, prodrug, or solvate thereof, is at least 80%, at least 85%, at least 90%, at least 92.5%, at least 95%, at least 97.5%, or at least 99% of the first active ingredient, by weight.

Pharmaceutically acceptable salts include any salt derived from an organic or inorganic acid. Examples of such salts include but are not limited to the following: salts of hydrobromic acid, hydrochloric acid, nitric acid, phosphoric acid and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1, 2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated by one skilled in the art that such pharmaceutically acceptable salts may be used in the formulation of a pharmacological composition. Such salts may be prepared by reacting the disclosed compound with a suitable acid in a manner known by those skilled in the art.

In preferred embodiments, the pharmaceutically acceptable salt for #1a is selected from the group consisting of: $Na^+$, $K^+$, $Mg^{2+}$, $Ca^{2+}$, $Zn^{2+}$ and $Al^{3+}$. In preferred embodiments, the pharmaceutically acceptable salt for #1 is selected from the group consisting of: $Na^+$, $K^+$, $Mg^{2+}$, $Ca^{2+}$, $Zn^{2+}$ and $Al^{3+}$.

The physical form of the pharmaceutical composition takes depend on a number of factors. For example, the desired method of administration, the physicochemical form taken by the disclosed compound or pharmaceutically acceptable salts thereof. Non-limiting examples of the physical forms include solid, liquid, gas, sol, gel, aerosol, etc. In some embodiments, the pharmaceutical composition consists of the disclosed compound or a pharmaceutically acceptable salt thereof, without any other additive.

In other embodiments, the pharmaceutical composition includes a second active ingredient of a distinct chemical formula from #1a or #1. In some aspects, the second active ingredient has the same or a similar molecular target as the target of #1a or #1. In other embodiments, the second active ingredient acts upstream of the molecular target of #1a or #1 with regard to one or more biochemical pathways. In yet other embodiments, the second active ingredient acts downstream of the molecular target of #1a or #1 with regard to one or more biochemical pathways. Pharmaceutical compositions that include the disclosed compound may be prepared using methodology well known in the pharmaceutical art.

In some embodiments, the pharmaceutical composition includes materials capable of modifying the physical form of a dosage unit. In a nonlimiting example, the composition includes a material that forms a coating that holds in the compound. Non-limiting examples of the materials include sugar, shellac, gelatin, and other inert coating agents.

The present invention is directed to a method of treating a histone deacetylase (HDAC) associated disease in a subject, comprising administering to the subject a composition selected from the group consisting of: #1a, #1, and pharmaceutically acceptable salt, ester, derivative, analog, prodrug, or solvate thereof.

Histone acetyltransferases (HAT) impact gene expression by controlling the coiling and uncoiling of DNA around histones. Histone acetyltransferases accomplish this by acetylating lysine residues in core histones leading to less compact and more transcriptionally active chromatin. In contrast, histone deacetylases (HDAC) remove the acetyl groups from lysine residues, leading to a more condensed and transcriptionally silenced chromatin. Reversible modification of the terminal tails of core histones constitutes the major epigenetic mechanism for remodeling of higher-order chromatin structure and controlling gene expression. HDAC inhibitors (HDI) block this action and can result in hyperacetylation of histones, thereby affecting gene expression. Thagalingam S., Cheng K H, Lee H J et al., *Ann. N.Y. Acad. Sci.* 983: 84-100, 2003; Marks P A. Richon V M, Rifkind R A, *J. Natl. Cancer Inst.* 92 (15) 1210-16, 2000; Dokmanovic M, Clarke C., Marks P A, *Mol. Cancer Res.* 5 (10) 981-989, 2007.

Histone deacetylase (HDAC) inhibitors are a new class of cytostatic agents that inhibit the proliferation of tumor cells in culture and in vivo by inducing cell cycle arrest, differentiation and/or apoptosis. Acetylation and deacetylation play important roles in the modulation of chromatin topology and the regulation of gene transcription. Histone deacetylase inhibitors induce the accumulation of hyperacetylated nucleosome core histones in many regions of chromatin but affect the expression of only a small subset of genes, leading to transcriptional activation of some genes, but repression of an equal or larger number of other genes. Non-histone proteins such as transcription factors are also the targets for acetylation with varying functional effects. Acetylation enhances the activity of some transcription factors such as the tumor suppressor p53 and the erythroid differentiation factor GATA-1 but may repress the transcriptional activity of others including T cell factor and the co-activator ACTR. Recent studies have shown that the estrogen receptor alpha (ERalpha) can be hyperacetylated in response to histone deacetylase inhibition, suppressing ligand sensitivity and regulating transcriptional activation by histone deacetylase inhibitors. Conservation of the acetylated ERalpha motif in other nuclear receptors suggests that acetylation may play an important regulatory role in diverse nuclear receptor signaling functions. A number of structurally diverse histone deacetylase inhibitors have shown potent antitumor efficacy with little toxicity in vivo in animal models. Several compounds are currently in early phase clinical development as potential treatments for solid and hematological cancers both as monotherapy and in combination with cytotoxics and differentiation agents.

The HDAC enzyme family constitutes a family of 18 genes that can be grouped into four subclasses; classes I-IV, based on their homology to respective yeast orthologs. HDACs, belonging to classes I, II and IV, comprise 11 members, namely HDAC isoforms 1-11, commonly referred to as the classical HDACs, are metal-dependent hydrolases. HDACs of class III, which comprise 7 members, known as sirtuins, namely Sirt 1-7, are NAD+-dependent hydrolases. Class I HDACs are nuclear proteins with ubiquitous tissue expression. Class II and IV HDACs are found in both the nucleus and cytoplasm and exhibit tissue-specific expression. The Class II HDAC family is further subdivided into subclasses IIA and IIB. Class IIA comprises isoforms HDAC4, HDAC5, HDAC7 and HDAC9 while Class IIB comprises isoforms HDAC6 and HDAC10. HDAC6 contains two tandem deacetylase domains and a C-terminal zinc finger domain. HDAC10 is structurally related to HDAC6 but has one additional catalytic domain. Table 1 represents the cellular location and tissue expression of classical HDACs (adapted from Witt, O. et al., Cancer Lett., 277:8-21 (2008)).

TABLE 1

Classical HDACs, Cellular Location and Tissue Expression

| Class | Isoform | Cellular Location | Tissue Expression |
|---|---|---|---|
| Class I | HDAC1 | Nuclear | Ubiquitous |
| | HDAC2 | Nuclear | Ubiquitous |
| | HDAC3 | Nuclear | Ubiquitous |
| | HDAC8 | Nuclear/cytoplasmic | Ubiquitous |
| Class IIA | HDAC4 | Nuclear/cytoplasmic | Heart, smooth muscles, brain |
| | HDAC5 | Nuclear/cytoplasmic | Heart, smooth muscle, brain |
| | HDAC7 | Nuclear/cytoplasmic | Heart, placenta, pancreas, smooth muscle |
| | HDAC9 | Nuclear/cytoplasmic | Smooth muscle, brain |
| Class IIB | HDAC6 | Cytoplasmic | Kidney, liver, heart, pancreas |
| | HDAC10 | Cytoplasmic | Spleen, kidney, liver |
| Class IV | HDAC11 | Nuclear/cytoplasmic | Heart, smooth muscle, kidney, brain |

HDACs play a significant role in both normal and aberrant cell proliferation and differentiation. HDACs have been associated with some disease states involving proliferation, including, but not limited to, cell proliferative diseases and conditions, such as various forms of cancer. (Reviewed in Witt, O. et al., Cancer Lett., 277:8-21 (2008); and Portella A. et al., Nat. Biotechnol., 28:1057-1068 (2010)). Class I and II HDACs have been identified as attractive targets for anticancer therapy. In particular, distinct class I and class II HDAC proteins are overexpressed in some cancers, including ovarian (HDAC1-3), gastric (HDAC2), and lung cancers (HDAC1 and 3), among others. Also, a possible correlation between HDAC8 and acute myeloid leukemia (AML) has been suggested. Concerning class II HDAC proteins, aberrant expression of HDAC6 is induced in some breast cancer cells. Based on their clinical effects, HDAC inhibitors have been identified that suppress tumor cell proliferation, induce cell differentiation, and upregulate crucial genes associated with anticancer effects. HDACs have also been implicated in various types of cancers (Bali P, et al., "Inhibition of histone deacetylase 6 acetylates and disrupts the chaperone function of heat shock protein 90: A novel basis for antileukemia activity of histone deacetylase inhibitors," J. Biol. Chem., 2005 280:26729-26734; Santo L. et al., "Preclinical activity, pharmacodynamic and pharmacokinetic properties of a selective HDAC6 inhibitor, ACY-1215, in combination with bortezomib in multiple myeloma," Blood, 2012, 119(11): 2579-89), autoimmune or inflammatory diseases (Shuttleworth, S. J., et al., Curr. Drug Targets, 11:1430-1438 (2010)), cognitive and neurodegenerative diseases (Fischer, A., et al., Trends Pharmacol. Sci., 31:605-617 (2010); Chuang, D.-M., et al., Trends Neurosci. 32:591-601 (2009)), fibrotic diseases (Pang, M. et al., J. Pharmacol. Exp. Ther., 335:266-272 (2010)), protozoal diseases (see, e.g., U.S. Pat. No. 5,922,837), and viral diseases (Margolis, D. M. et al., Curr. Opin. HIV AIDS, 6:25-29 (2011)).

In recent years, there has been an effort to develop HDAC inhibitors as cancer treatments and/or as an adjunct therapy. Mark P A. et al. *Expert Opinion on Investigational Drugs* 14 (12): 1497-1511 (2005). The exact mechanisms by which the compounds may work are unclear, but epigenetic pathways have been studied to help elucidate the exact biological pathways. Claude Monneret, *Anticancer Drugs* 18(4):363-370 2007. For example, HDAC inhibitors have been shown to induce p21 (WAFI) expression, a regulator of p53's tumor suppressor activity. Rochon V M. et al., *Proc. Natl. Acad. Sci. U.S.A.* 97(18): 10014-10019, 2000. HDACs are involved in the pathway by which the retinoblastoma protein (pRb) suppresses cell proliferation. The pRb protein is part of a complex that attracts HDACs to the chromatin so that it will deacetylate histones. Brehm A. et al., *Nature* 391 (6667): 597-601, 1998. HDAC1 negatively regulates the cardiovascular transcription factor Kruppel-like factor 5 through direct interaction. Matsumura T. et al., *J. Biol. Chem.* 280 (13): 12123-12129, 2005. Estrogen is well-established as a mitogenic factor implicated in the tumorigenesis and progression of breast cancer via its binding to the estrogen receptor alpha (ERα). Recent data indicate that chromatin inactivation mediated by HDAC and DNA methylation is a critical component of ERα silencing its human breast cancer cells. Zhang Z. et al., *Breast Cancer Res. Treat.* 94(1): 11-16, 2005.

Typically, the method comprises administering to a subject any one of the disclosed compounds, or pharmaceutically acceptable salt, ester, derivative, analog, prodrug, or solvate thereof.

Non-limiting examples of the disease include: a cell proliferative disease (e.g., cancer), an autoimmune disorder, an inflammatory disorder, a neurodegenerative disease, and combinations thereof, etc.

In some embodiments, the cell proliferative disease is cancer. Non-limiting examples of cancer include: acute lymphocytic leukemia (ALL), acute myeloid leukemia (AML), acute promyelocytic leukemia (APL), breast cancer, chronic myeloid leukemia (CML), colon cancer, diffuse large B-cell lymphoma (DLBCL), gastrointestinal stromal tumor (GIST), glioblastoma (GBM), hepatocellular carcinoma, Hodgkin's lymphoma, leukemia, lung cancer, multiple myeloma, non-Hodgkin's lymphoma, non-small cell lung cancer (NSCLC), neuroblastoma, ovarian cancer, pancreatic ductal adenocarcinoma, peripheral T-cell lymphoma, prostate cancer, uterine cancer, Waldenstrom myeloma, and combinations thereof, etc.

In some embodiments, the cancer is selected from the group consisting of: ovarian cancer, prostate cancer, lung cancer, acute myeloid leukemia, multiple myeloma, bladder carcinoma, renal carcinoma, breast carcinoma, colorectal carcinoma, neuroblastoma, melanoma, gastric cancer, and combinations thereof. In some aspects, the compound of formula (I) inhibits cancer cell proliferation, induces cancer cell death, or both.

Non-limiting examples of the autoimmune disorder or inflammatory disorder include: airway hyperresponsiveness, Crohn's disease, inflammatory bowel disease, multiple sclerosis, psoriasis, rheumatoid arthritis, systemic lupus erythematosus, type 1 diabetes, ulcerative colitis, and combinations thereof, etc.

Non-limiting examples of the neurodegenerative disorder include: Alzheimer's disease (AD), amyotrophic lateral sclerosis (ALS), cerebral ischemia, Huntington's disease (HD), Parkinson's disease (PD), spinal muscular atrophy, and combinations thereof, etc.

In some aspects, the disease is associated with HDAC1, HDAC2, HDAC3, HDAC4, HDAC5, HDAC6, HDAC7, HDAC8, HDAC9, HDAC10, HDAC11, or combinations thereof. In other aspects, the HDAC-associated disease is associated with HDAC1, HDAC2, HDAC3, HDAC6, HDAC10, or combinations thereof. In yet other aspects, the HDAC-associated disease is associated with HDAC1, HDAC2, HDAC6, or combinations thereof.

In certain more specific aspects of the invention, the composition reduces cancer cell expansion with a half maximal inhibitory concentration ($IC_{50}$) of 0.0001-4 µM, or any number range in between, e.g., 0.0002-4 µM, 0.0002-3.5 µM, 0.0005-3.5 µM, 0.0005-3 µM, 0.001-3 µM, 0.001-2.5 µM, 0.002-2.5 µM, 0.002-2 µM or 0.005-2 µM etc.

In other aspects, the composition reduces cancer cell expansion with a half maximal inhibitory concentration ($IC_{50}$) of 0.001-10 µM, or any number range in between, e.g., 0.001-8 µM, 0.002-8 µM, 0.002-6 µM, 0.003-6 µM, 0.003-4 µM, 0.005-4 µM, 0.005-2 µM or 0.01-2 µM etc. In yet other aspects, the composition reduces cancer cell expansion with a half maximal inhibitory concentration ($IC_5O$) of 0.02-10 µM, or any number range in between, e.g., 0.05-10 µM, 0.05-9 µM, 0.1-9 µM, 0.1-8 µM, 0.2-8 µM, 0.2-7 µM, 0.4-7 µM or 0.4-6 µM etc. In further aspects, the compound of formula (I) inhibits the activity of the HDAC isoform with a half maximal inhibitory concentration ($IC_{50}$) of lower than 1 µM, lower than 0.5 µM, lower than 0.2 µM, lower than 0.1 µM, lower than 0.01 µM, lower than 0.001 µM, etc.

In some embodiments, the composition reduces cancer cell expansion by at least 90%, at least 80%, at least 70%, at least 60%, at least 50%, at least 40%, at least 30%, at least 20%, or at least 10%. In other embodiments, the composition reduces cancer cell expansion by 10-100%, or any percent range in between, e.g., 10-90%, 15-90%, 30%-90%, 15-80%, 20-80%, 30%-80%, 20-70%, 25-70%, 30%-70%, 25-60%, 30-60%, or 30-50%, etc.

In some embodiments, the composition inhibits the histone deacetylating activity of the HDAC isoform by at least 90%, at least 80%, at least 70%, at least 60%, at least 50%, at least 40%, at least 30%, at least 20%, or at least 10%. In other embodiments, the composition inhibits the histone deacetylating activity of the HDAC isoform by 10-100%, or any percent range in between, e.g., 10-90%, 15-90%, 30%-90%, 15-80%, 20-80%, 30%-80%, 20-70%, 25-70%, 30%-70%, 25-60%, 30-60%, or 30-50%, etc.

In some aspects, the composition is administered at 10-400 mg/kg, or any number in between, e.g., 10-350 mg/kg, 20-350 mg/kg, 20-300 mg/kg, 30-300 mg/kg, 30-250 mg/kg, 40-250 mg/kg, 40-200 mg/kg, 50-200 mg/kg, 50-150 mg/kg, 60-150 mg/kg, or 60-100 mg/kg, etc.

In other aspects, the composition is administered about every 4, 8, 12, 16, or 24 hours. In yet other aspects, the composition is administered every 1-24 hours, or any number in between, e.g., 2-24 hours, 2-18 hours, 3-18 hours, 3-16 hours, 4-16 hours, 4-12 hours, 5-12 hours, 5-8 hours, etc.

In some embodiments, the composition further comprises a second active ingredient selected from the group consisting of a chemotherapy drug, an agent that enhances antigen presentation ("antigen-presentation combination"), an agent that enhances an effector cell response ("effector cell combination"), an agent that decreases tumor immunosuppression ("anti-tumor immunosuppression combination"), and combinations thereof.

Non-limiting examples of the chemotherapy drug include: pomalidomide, or dexamethasone, etc.

Combination with Kinase Inhibition

One particularly attractive target for small-molecule modulation, with respect to anti-proliferative activity is MEK. Inhibition of MEK1 (MAPK/ERK Kinase) is a promising strategy to control the growth of tumors that are dependent on aberrant ERK/MAPK pathway signaling. The MEK-ERK signal transduction cascade is a conserved pathway, which regulates cell growth, proliferation, differentiation, and apoptosis in response to growth factors, cytokines, and hormones. This pathway operates downstream of Ras which is often upregulated or mutated in human tumors. It has been demonstrated that MEK is a critical effector of Ras function. The ERK/MAPK pathway is upregulated in 30% of all tumors and oncogenic activating mutations in K-Ras and B-Raf have been identified in 22% and 18% of all cancers respectively. It has been reported that a large portion of human cancers, including 66% (B-Raf) of malignant melanomas, 60% (K-Ras) and 4% (B-Raf) of pancreatic cancers, 50% of colorectal cancers (colon, in particular, K-Ras: 30%, B-Raf: 15%), 20% (K-Ras) of lung cancers, 27% (B-Raf) papillary and anaplastic thyroid cancer, and 10-20% (B-Raf) of endometriod ovarian cancers, harbor activating Ras and Raf mutations. It has been shown that inhibition of the ERK pathway, and in particular inhibition of MEK kinase activity, results in anti-metastatic and anti-angiogenic effects largely due to a reduction of cell-cell contact and motility as well as downregulation of vascular endothelial growth factor (VEGF) expression. Furthermore, expression of dominant negative MEK, or ERK reduced the transforming ability of mutant Ras as seen in cell culture and in primary and metastatic growth of human tumor xenografts in vivo. Therefore, the MEK-ERK signal transduction pathway is an appropriate pathway to target for therapeutic intervention.

Non-limiting examples of agents that inhibit MEK kinases may be selected from the group consisting of N—((S)-2,3-Dihydroxy-propyl)-3-(2-fluoro-4-iodo-phenylamino)-isonicotinamide, CI-1040, PD035901, AZD6244, GSK1 120212, GDC-0973, U0126, XL-518, ARRY-162, ARRY-300, PD184161, PD184352, PD0325901, ARRY-142886 (AZD6244), R04927350, PD0325901, CIP-1374, TAK-733, CH4987655, RDEA119, trametinib, cobimetinib, refametinib, selumetinib, binimetinib, PD098059, U0126, CH4987655, CH5126755 and GDC623, or pharmaceutically acceptable salts and a combination thereof.

Antigen-Presentation Combination Non-limiting examples of the agent that enhances antigen presentation include: an agent that enhances antigen presentation, an agent that enhances lysis of tumor cells, an agent that stimulates a phagocyte, an agent that disinhibits a phagocyte, an agent that activates a dendritic cell, an agent that activates a macrophage (e.g., a macrophage I), an agent that recruits a dendritic cell, or an agent that recruits a macrophage (e.g., a macrophage I), or a vaccine, etc. In certain non-limiting aspects, the agent that enhances antigen presentation enhances tumor antigen presentation.

Non-limiting examples of the vaccine include: a cell-based vaccine (e.g., a dendritic cell-based vaccine such as Provenge®), or an antigen-based vaccine (e.g., IL-2 in combination with MUC1), etc. A non-limiting example of the agent that enhances lysis of tumor cells is an oncolytic virus. A non-limiting example of the agent that stimulates a phagocyte is a Type I interferon (IFN) activator, for example, a TLR agonist, or a RIG-I-like receptor agonist (RLR), etc. Non-limiting examples of the agent that activates and/or recruits a dendritic cell or a macrophage include: a bi-specific cell engager or a tri-specific cell engager, etc.

In some embodiments, the agent that enhances antigen presentation is selected from the group consisting of: an agonist of Stimulator of Interferon Genes (a STING agonist), an agonist of a Toll-like receptor (TLR), a TIM-3 modulator, a vascular endothelial growth factor receptor (VEGFR) inhibitor, a c-Met inhibitor, a TGFb inhibitor, an IDO/TDO inhibitor, an A2AR antagonist, an oncolytic virus, a vaccine, a bi-specific cell engager, a tri-specific cell engager, a bi-specific antibody molecule, a tri-specific antibody molecule, an IDO/TDO inhibitor, and combinations thereof.

Non-limiting examples of TLR include: an agonist of TLR-3, TLR-4, TLR-5, TLR-7, TLR-8, or TLR-9, etc. A non-limiting example of the TIM-3 modulator is an anti-TIM-3 antibody molecule. A non-limiting example of the TGFb inhibitor is an anti-TGFb antibody. A non-limiting example of the vaccine is a scaffold vaccine. In some aspects, the oncolytic virus expresses a cytokine, for example, GM-CSF, or a CSF (e.g., CSF1, or CSF2), etc. Non-limiting examples of bi- or tri-specific cell engager include: a bi- or tri-specific antibody molecule to CD47 and CD19, with or without an Fc domain.

Effector Cell Combination

Non-limiting examples of the agent that enhances an effector cell response include: a lymphocyte activator, an agent that activates and/or disinhibits a tumor infiltrating lymphocyte (TIL), an NK cell modulator, an interleukin or an interleukin variant, a bi- or tri-specific cell engager, an NK cell therapy, a vaccine that induces NK cells and an antigen/immune stimulant, an immunomodulator, a T cell modulator, a bispecific T cell engager, an inhibitor of IAP (Inhibitor of Apoptosis Protein), or an inhibitor of target of rapamycin (mTOR), etc.

Non-limiting examples of the lymphocyte activator include: an NK cell activator, or a T cell activator, etc. Non-limiting examples of the tumor infiltrating lymphocyte (TIL) include: an NK cell, or a T cell, etc. A non-limiting example of the NK cell modulator is a modulator (e.g., an antibody molecule) of an NK receptor, for example, a modulator of NKG2A, KIR3DL, NKp46, MICA, CEACAMI, or combinations thereof, etc. Non-limiting examples of the interleukin include: IL-2, IL-15, IL-21, IL-13R, IL-12 cytokine, or a combination thereof, etc. Non-limiting examples of the bi- or tri-specific cell engager include: a bispecific antibody molecule of NKG2A and CD138, or a bispecific antibody molecule of CD3 and TCR, etc. Non-limiting examples of the immunomodulator include: an activator of a costimulatory molecule, or an inhibitor of an immune checkpoint molecule, etc.

In some embodiments, the T cell modulator is a T cell modulator chosen from an inhibitor of a checkpoint inhibitor. Non-limiting examples of the T cell modulator chosen from an inhibitor (e.g., an antibody) of a checkpoint inhibitor include: an inhibitor of PD-1, an inhibitor of PD-L1, an inhibitor of TIM-3, an inhibitor of LAG-3, an inhibitor of VISTA, an inhibitor of diacylglycerol kinases (DKG)-alpha, an inhibitor of B7-H3, an inhibitor of B7-H4, an inhibitor of TIGIT, an inhibitor of CTLA4, an inhibitor of BTLA, an inhibitor of CD160, an inhibitor of TIM1, an inhibitor of IDO, an inhibitor of LAIR1, an inhibitor of IL-12, or a combination thereof, etc.

In other embodiments, the T cell modulator is a T cell modulator chosen from an agonist or an activator of a costimulatory molecule. Non-limiting examples of the T cell modulator chosen from an agonist or an activator of a costimulatory molecule include: an agonistic antibody, an antigen-binding fragment thereof, or a soluble fusion, etc. of GITR, OX40, ICOS, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand, etc. A non-limiting example of the bispecific T cell engager is a bispecific antibody molecule that binds to CD3 and a tumor antigen, for example, Epidermal Growth Factor Receptor (EGFR), PSCA, PSMA, EpCAM, or HER2, etc.

Anti-Tumor Immunosuppression Combination

Non-limiting examples of the agent that decreases tumor immunosuppression include: an agent that modulates the activity and/or level of $T_{reg}$, macrophage 2, and/or MDSCs, an agent that increases M2 polarization, $T_{reg}$ depletion, and/or T cell recruitment.

Non-limiting examples of the agent that decreases tumor immunosuppression include: an immunomodulator, a CSF-1/1R inhibitor, an IL-17 inhibitor, an IL-1.beta. inhibitor, a CXCR2 inhibitor, an inhibitor of a phosphoinositide 3-kinase, a BAFF-R inhibitor, a MALT-1/BTK inhibitor, a JAK inhibitor, a CRTH2 inhibitor, a VEGFR inhibitor, an IL-15 or a variant thereof, a CTLA-4 inhibitor, an IDO/TDO inhibitor, an A2AR antagonist, a TGFb inhibitor, or a PFKFB3 inhibitor, an inhibitor of an immune checkpoint molecule, etc.

Non-limiting examples of the immunomodulator include: an activator of a costimulatory molecule (e.g., a GITR agonist), or an inhibitor of an immune checkpoint molecule (e.g., PD-1, PD-L1, LAG-3, T1M-3, or CTLA-4, etc.), etc. A non-limiting example of the CSF-1/1R inhibitor is an inhibitor of macrophage colony-stimulating factor (M-CSF). A non-limiting example of the inhibitor of a phosphoinositide 3-kinase is PI3K, e.g., PI3K.gamma, or P13K.delta, etc. Non-limiting examples of the inhibitor of an immune checkpoint molecule include: an inhibitor of PD-1, an inhibitor of PD-L1, an inhibitor of LAG-3, an inhibitor of TIM-3, an inhibitor of CEACAM (e.g., CEACAM-1, CEACAM-3, and/or CEACAM-5, etc.), or an inhibitor of CTLA-4, etc.

In some embodiments, the second active ingredient comprises one or more therapeutic agents that enhance antigen presentation, one or more therapeutic agents that enhance an effector cell response, and/or one or more therapeutic agents that decrease tumor immunosuppression.

In certain embodiments, the second active ingredient is selected from the group consisting of: a STING agonist, a TLR agonist (e.g., a TLR7 agonist), a TIM-3 modulator (e.g., a TIM-3 inhibitor), a GITR modulator (e.g., a GITR agonist), a PD-1 inhibitor (e.g., an anti-PD-1 antibody molecule), a PD-L1 inhibitor, a CSF-1/1R inhibitor (e.g., an M-CSF inhibitor), an IL-17 inhibitor, an IL-1.beta. inhibitor, and combinations thereof.

Non-limiting examples of the histone deacetylase (HDAC)-associated disease treated by the second therapeutic agent and #1a, N-hydroxy-2-(2-(4-methoxyphenyl)butanamido)thiazole-5-carboxamide, or pharmaceutically acceptable salts thereof include: breast cancer, colorectal cancer, head and neck cancer, hematological cancer, leukemia, liver cancer, lung cancer, melanoma, myeloma, non-Hogdkin's lymphoma, pancreatic cancer, prostate cancer, renal cancer, or metastatic lesion of cancer, etc.

The route of administration may be affected by the physical form of the invention and the disorder to be treated. In some embodiments, the pharmaceutical composition is prepared as a gas. In other embodiments, the pharmaceutical composition is prepared as an aerosol. Aerosols encompass a variety of systems including colloids and pressurized packages. Non-limiting examples of delivery of a composition in this form include propulsion of the pharmaceutical composition through liquefied gas, through other compressed gas, and using a suitable pump system. Aerosols may be delivered in single phase, bi-phasic, or tri-phasic systems.

The present invention is further directed to a pharmaceutical composition for treating a histone deacetylase (HDAC)-associated disease. Typically, the pharmaceutical composition comprises an active ingredient and a pharmaceutically acceptable carrier. The active ingredient comprises at least a first active ingredient selected from the group consisting of: (S)—N-hydroxy-2-(2-(4-methoxyphenyl)butanamido)thiazole-5-carboxamide, N-hydroxy-2-(2-(4-methoxyphenyl) butanamido)thiazole-5-carboxamide, and pharmaceutically acceptable salt, ester, derivative, analog, prodrug, or solvate thereof. In some non-limiting aspects, the first active ingredient forms an amorphous dispersion. In some embodiments, the pharmaceutically acceptable salt is selected from the group consisting of: aluminum, calcium, magnesium, potassium, sodium, zinc, and combinations thereof. In other embodiments, the pharmaceutical composition further comprises a second active ingredient (in a final dosage form). In some aspects, the second active ingredient comprises a DNA methyltransferase inhibitor, a bromodomain inhibitor, or both.

In some aspects, the pharmaceutically acceptable carrier is selected from the group consisting of: a pharmaceutical polymer carrier, a processing agent, a surfactant, and a combination thereof.

Non-limiting examples of the pharmaceutical polymer carrier include: a cellulosic pharmaceutical polymer, a cross-linked pharmaceutical polymer, a high melt viscosity pharmaceutical polymer, a non-ionic pharmaceutical polymer, a non-ionic, cellulosic pharmaceutical polymer, a non-ionic, water-soluble pharmaceutical polymer, a thermally labile pharmaceutical polymer, a water-soluble pharmaceutical polymer, or a water-soluble, cellulosic pharmaceutical polymer, etc.

Non-limiting examples of the non-ionic pharmaceutical polymer carrier include: a cellulosic polymer, a water-soluble polymer, or a cellulosic and water-soluble polymer, etc. Non-limiting examples of non-ionic, water-soluble pharmaceutical polymers include: hydroxyethylcellulose, hydroxypropylcellulose, hydroxypropyl methylcellulose, poly(vinyl acetate)-co-poly(vinylpyrrolidone) copolymer, poly(vinyl alcohol), polyvinyl caprolactam-polyvinyl acetate-polyethylene glycol graft copolymer, poly(vinlypyrrolidone), or sodium carboxymethyl-cellulose, etc.

Non-limiting examples of cross-linked pharmaceutical polymers include: carbomer, crospovidone, polycarbophil, or croscarmellose sodium, etc.

Non-limiting examples of the pharmaceutical polymer include: cellulose acetate butyrate, cellulose acetate phthalate, cellulose acetate trimelletate, dimethylaminoethyl methacrylate-methacrylic acid ester copolymer, ethylacrylate-methylmethacrylate copolymer, ethylcellulose, hydroxyethylcellulose, hydroxypropylcellulose, hydroxypropyl methylcellulose, hydroxypropylmethylcellulose acetate succinate, hydroxypropylmethylcellulose phthalate, poly(butyl methacylate-co-(2-dimethylaminoethyl) methacrylate-co-methyl methacrylate) 1:2:1, poly(ethylene glycol), poly(ethylene oxide), poly(methacrylate ethylacrylate) (1:1) copolymer, poly(methacrylate methylmethacrylate) (1:1) copolymer, poly(methacrylate methylmethacrylate) (1:2) copolymer, poly(vinyl acetate)-co-poly(vinylpyrrolidone) copolymer, poly(vinyl acetate) phthalate, poly(vinyl alcohol), polyvinyl caprolactam-polyvinyl acetate-polyethylene glycol graft copolymer, poly(vinylpyrrolidone), or sodium carboxymethyl-cellulose.

A non-limiting example of processing agent is a plasticizer.

Non-limiting examples of the surfactants include: dioctyl sodium sulphosuccinate, glycerol polyethylene glycol oxystearate-fatty acid glycerol polyglycol esters-polyethylene glycols-glycerol ethoxylate, glycerolpolyethylene glycol ricinoleate-fatty acid esters of polyethylene glycol-polyethylene glycols-ethoxylated glycerol, polyoxyethylene (20) sorbitan monooleate, sodium dodecyl sulfate, sorbitan laurate, or vitamin E TPGS (also known as d-α-Tocopheryl polyethylene glycol 1000 succinate).

In some aspects, the pharmaceutical composition is a composite. In some embodiments, the pharmaceutical composition is a melt blended pharmaceutical composite. In further embodiments, the pharmaceutical composition is a homogenous, heterogeneous, or heterogeneously homogenous composition. In other aspects, the pharmaceutical composition is formulated into an oral dosage form. Non-limiting examples of oral dosage forms include: a tablet, a capsule, or a sachet, etc.

The present disclosure also relates to a method of making the pharmaceutical composition. Typically, the method comprises mixing an active ingredient with a pharmaceutically acceptable carrier in a thermokinetic mixer for a length of time, wherein the active ingredient comprises at least a first active ingredient selected from #1a, #1, and a pharmaceutically acceptable salt, ester, derivative, analog, prodrug, or solvate thereof, and the thermokinetic compounding of the active ingredient and the pharmaceutically acceptable carrier form a melt blended pharmaceutical composite.

In some aspects of the method of making the pharmaceutical composition, the active ingredient further comprises a second active ingredients (other than #1a), for example, a DNA methyltransferase inhibitor, a bromodomain inhibitor, or both, in a final dosage form.

Non-limiting examples of the length of time of the mixing include: less than 1,200 seconds, less than 900 seconds, less than 600 seconds, less than 500 seconds, less than 400 seconds, less than 350 seconds, less than 250 seconds, less than 200 seconds, or less than 150 seconds. In preferred embodiments, the length of time of the mixing is less than 300 seconds.

In some aspects of the method, the mixing is performed at a defined temperature. For example, less than about 400° C., less than about 375° C., less than about 350° C., less than about 325° C., less than about 300° C., less than about 275° C., less than about 225° C., or less than about 200° C., etc. In preferred embodiments, the mixing is performed at less than about 250° C.

In some aspects, the pharmaceutical composition is dissolved in a pharmaceutically acceptable solvent or a mixture of more than one solvent. The solvent delivers a sufficient quantity of the disclosed compound to treat the HDAC-associated disease without serious complications in the subject. Non-limiting examples of the solvents include pyridine, chloroform, propan-1-ol, ethyl oleate, ethyl lactate, ethylene oxide, water, or ethanol, etc.

The pharmaceutical composition may take any number of formulations depending on the physicochemical form of the composition and the type of administration. Non-limiting examples of the forms of the composition include solution, suspension, emulsion, tablet, pill, pellet, or capsule, etc. Non-limiting examples of the capsules include: liquid, powder, sustained-release formulation, directed release formulation, lyophylate, suppository, emulsion, aerosol, spray, granule, powder, syrup, or elixir, etc.

Examples of suitable pharmaceutical carriers are described in "Remington's Pharmaceutical Sciences" by E. W. Martin, hereby incorporated by reference in its entirety.

Non-limiting examples of methods of administrations include oral and parenteral administration. Non-limiting examples of parenteral administrations include intradermal, intramuscular, intraperitoneal, intravenous, subcutaneous, intranasal, epidural, sublingual, intramsal, intracerebral, iratraventricular, intrathecal, intravaginal, transdermal, rectal, inhalation, and topical (e.g., to ear, nose, eye, or skin), etc.

In some aspects, administration uses a infusion technique selected from the group consisting of: infusion or bolus injection, and absorption through epithelial or mucocutaneous linings (e.g., oral mucosa, rectal, and intestinal mucosa). In other aspects, the composition for parenteral administration is enclosed in an ampoule, a disposable syringe, or a multiple-dose vial made of glass, plastic, or another material.

In some embodiments, administration is systemic. In other embodiments, administration is local, i.e., administration to the area in need of treatment. Non-limiting examples of local administration include local infusion during surgery, topical application, and local injection (by a catheter, a suppository, or an implant). In some aspects, administration is direct injection at the site or former site of cancer, tumor, precancerous tissue. In other aspects, administration is direct injection into the central nervous system, for example, by intraventricular or intrathecal injection. In yet other aspects, intraventricular injection is facilitated by an intraventricular catheter. In further aspects, the intraventricular catheter is attached to a reservoir (e.g., an Ommaya reservoir). In some embodiments, pulmonary administration is used. Non-limiting examples of pulmonary administrations include use of an inhaler or nebulizer, formulation with an aerosolizing agent, and perfusion in a fluorocarbon or synthetic pulmonary surfactant. In other embodiments, the pharmaceutical composition is delivered in the context of a natural or synthetic vesicle. In yet other embodiments, the pharmaceutical composition is delivered a liposome.

In some aspects, the pharmaceutical composition is prepared by dissolving the disclosed compound with water so as to form a solution. In other aspects, a surfactant is added to facilitate the formation of a homogeneous solution or suspension. Surfactants include any complex capable of non-covalent interaction with the disclosed compound so as to facilitate dissolution or homogeneous suspension of the compound.

In yet other aspects, the pharmaceutical composition is prepared in a form that facilitates topical or transdermal administration, for example, in the form of solution, emulsion, ointment, gel base, transdermal patch, or iontophoresis device. Non-limiting examples of bases used in such compositions include opetrolatum, lanolin, polyethylene glycol, beeswax, mineral oil, diluent (e.g., water or alcohol), emulsifier, stabilizer, thickening agent, etc.

In certain embodiments, the invention is directed to a method of inhibiting an HDAC isoform in one or more various cells. The method comprising contacting the cell with an effective amount of any one of the disclosed compounds of formula (I), or a pharmaceutically acceptable salt form thereof.

In some embodiments, the cell is selected from the group consisting of: a cancer cell, a neuronal cell, a cell of the immune system, a cell of the circulatory system, and combinations thereof. In other embodiments, the cell is a cancer cell. In yet other embodiments, the cell is a neuronal cell. In further embodiments, the cell is a cell of the immune system. In yet further combinations, the cell is a cell of the circulatory system.

Non-limiting examples of the cancer cell include: an acute lymphocytic leukemia (ALL) cell, an acute myeloid leukemia (AML) cell, an acute promyelocytic leukemia (APL) cell, a breast cancer cell, a chronic myeloid leukemia (CML) cell, a colon cancer cell, a diffuse large B-cell lymphoma (DLBCL) cell, a gastrointestinal stromal tumor (GIST) cell, a glioblastoma (GBM) cell, a hepatocellular carcinoma cell, a Hodgkin lymphoma cell, a leukemia cell, a lung cancer cell, a multiple myeloma cell, a non-Hodgkin's lymphoma cell, a non-small cell lung cancer (NSCLC) cell, a neuroblastoma cell, an ovarian cancer cell, a pancreatic ductal adenocarcinoma cell, a peripheral T-cell lymphoma cell, a prostate cancer cell, a uterine cancer cell, and a Waldenstrom myeloma cell, etc.

In some embodiments, the HDAC isoform is selected from the group consisting of: HDAC1, HDAC2, HDAC3, HDAC4, HDAC5, HDAC6, HDAC1, HDAC8, HDAC9, HDAC10, HDAC11, and combinations thereof. In other embodiments, the HDAC isoform is selected from the group consisting of: HDAC1, HDAC2, HDAC3, HDAC6, HDAC10, and combinations thereof. In yet other embodiments, the HDAC isoform is selected from the group consisting of: HDAC1, HDAC3, HDAC6, and combinations thereof.

In some aspects, the compound of formula (I) inhibits the histone deacetylating activity of the HDAC isoform with a half maximal inhibitory concentration ($IC_{50}$) of 0.0001-4 µM, or any number range in between, e.g., 0.0002-4 µM, 0.0002-3.5 µM, 0.0005-3.5 µM, 0.0005-3 µM, 0.001-3 µM, 0.001-2.5 µM, 0.002-2.5 µM, 0.002-2 µM or 0.005-2 µM etc. In other aspects, the compound of formula (I) inhibits the histone deacetylating activity of the HDAC isoform with a half maximal inhibitory concentration ($IC_{50}$) of 0.001-10 µM, or any number range in between, e.g., 0.001-8 µM, 0.002-8 µM, 0.002-6 µM, 0.003-6 µM, 0.003-4 µM, 0.005-4 µM, 0.005-2 µM or 0.01-2 µM etc. In yet other aspects, the compound of formula (I) inhibits the histone deacetylating activity of the HDAC isoform with a half maximal inhibitory concentration ($I_{C50}$) of 0.02-10 µM, or any number range in between, e.g., 0.05-10 µM, 0.05-9 µM, 0.1-9 µM, 0.1-8 µM, 0.2-8 µM, 0.2-7 µM, 0.4-7 µM or 0.4-6 µM etc. In further aspects, the compound of formula (I) inhibits the activity of the HDAC isoform with a half maximal inhibitory concentration ($IC_{50}$) of lower than 1 µIVI, lower than 0.5 µM, lower than 0.2 µM, lower than 0.1 µM, lower than 0.01 µM, lower than 0.001 µM, etc.

In some embodiments, the compound inhibits the histone deacetylating activity of the HDAC isoform by at least 90%, at least 80%, at least 70%, at least 60%, at least 50%, at least 40%, at least 30%, at least 20%, or at least 10%. In other embodiments, the compound inhibits the histone deacetylating activity of the HDAC isoform by 10-100%, or any percent range in between, e.g., 10-90%, 15-90%, 30%-90%, 15-80%, 20-80%, 30%-80%, 20-70%, 25-70%, 30%-70%, 25-60%, 30-60%, or 30-50%, etc.

In some embodiments, the compound of formula (I) inhibits the histone deacetylating activity of the HDAC isoform, thereby inhibits cell proliferation, induces cell death, or both.

In some aspects, the method is performed in vitro. A non-limiting example is a screening assay using the compound of formula (I) as a positive control, a standard, or both to measure the activity of an unknown compound in inhibiting HDAC.

In some aspects, the method is performed in vivo, thereby inhibiting the HDAC isoform in a subject. The contacting is achieved by administering the compound, or a pharmaceutically acceptable salt form thereof, in an amount effective to inhibit the HDAC isoform. In other aspects, the subject is a human, e.g., a patient.

A cancer cell includes a cell derived from a tumor, neoplasm, cancer, precancer, cell line, or any other sources that is potentially capable of unlimited expansion and growth. In some aspects, the cancer cell is derived from a naturally occurring source. In other aspects, the cancer cell is artificially created. In some embodiments, the cancer cell is capable of invasion into a tissue and metastasis when placed into an animal host. Cancer cells further encompass any malignant cells that have invaded other tissues, metastasized, or both. In some aspects, one or more cancer cells of an organism is referred to as a cancer, a tumor, a neoplasm, a growth, a malignancy, or another term used in the art describing cells in a cancerous state.

Expansion of a cancer cell includes any process that results in an increase in the number of individual cells derived from a cancer cell. Expansion of a cancer cell may result from mitotic division, proliferation, or any other form of expansion of a cancer cell, whether in vitro or in vivo. Expansion of a cancer cell further encompasses invasion and metastasis. A cancer cell may be in physical proximity to cancer cells from the same clone or from different clones that may or may not be genetically identical to it. Such aggregations may take the form of a colony, tumor or metastasis, any of which may occur in vivo or in vitro. Slowing the expansion of the cancer cell may be brought about either by inhibiting cellular processes that promote expansion or by bringing about cellular processes that inhibit expansion. Processes that inhibit expansion include processes that slow mitotic division and processes that promote cell senescence or cell death. Examples of specific processes that inhibit expansion include: caspase dependent and independent pathways, autophagy, necrosis, apoptosis, and mitochondrial dependent and independent processes and further include any such processes yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per os, parenteral, or any other of the methods of administration; or the activation or inhibition of cells that in turn have effects on the cancer cells such as immune cells (e.g., macrophages and $CD8^+$ T cells) or endothelial cells that may differentiate into blood vessel structures in the process of angiogenesis or vasculogenesis.

Determination of an effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The effective amount of the disclosed compound that results in a slowing of expansion of the cancer cells would be a concentration at or near the target tissue that is effective in slowing cellular expansion in neoplastic cells, with a lesser effect (up to and including no effect) on non-neoplastic cells, including non-neoplastic cells previously or concurrently exposed to radiation or chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease.

The addition of a therapeutically effective amount of the disclosed compound encompasses any method of dosing of a compound. Dosing of the disclosed compound may include single of multiple administrations of any of a number of pharmaceutical compositions that include the disclosed compound as an active ingredient. Examples include a single administration of a slow release composition, a course of a treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the disclosed compound may be administered prior to, concurrently with, or after administration of a second pharmaceutical composition that may or may not include the compound. If the compositions are administered concurrently, they are administered within one minute of each other. If not administered concurrently, the second pharmaceutical composition may be administered a period of one or more minutes, hours, days, weeks, or months before or after the pharmaceutical composition that includes the compound Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more-unit dosages of the compound. The unit dosage would be enclosed in a preferably sterile container and would be comprised of the disclosed compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage.

Pharmaceutical compositions including the disclosed compound may be used in methods of treating cancer. Such methods involve the administration of a therapeutic amount of a pharmaceutical composition that includes the disclosed compound and/or a pharmaceutically acceptable salt thereof to a mammal, preferably a mammal in which a cancer has been diagnosed.

A therapeutic amount further includes an amount of that results in the prevention of progression of the cancer to a neoplastic, malignant or metastatic state. Such preventative use is indicated in conditions known or suspected of preceding progression to neoplasia or cancer, in particular, where non-neoplastic cell expansion consisting of hyperplasia, metaplasia, or dysplasia has occurred (for review of such abnormal expansion conditions, see Robbins and Angell, 1976, *Basic Pathology,* 2d Ed., W. B. Saunders Co., Philadelphia, pp. 68-79). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell expansion in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer and is found mainly in the epithelia; it is the most disorderly form of non-neoplastic cell expansion, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively, or in addition to the presence of abnormal cell expansion characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype). Further examples include leukoplakia, in which a benign-appearing hyperplastic or dysplastic lesion of the epithelium, or Bowen's disease, a carcinoma in situ, are pre-neoplastic lesions indicative of the desirability of prophylactic intervention. In another example, fibrocystic disease including cystic hyperplasia, mammary dysplasia, adenosis, or benign epithelial hyperplasia is indicative of the desirability of prophylactic intervention.

In some aspects of the invention, use of the disclosed compound may be determined by one or more physical factors such as tumor size and grade or one or more molecular markers and/or expression signatures that indicate prognosis and the likely response to treatment with the compound. For example, determination of estrogen (ER) and progesterone (PR) steroid hormone receptor status has become a routine procedure in assessment of breast cancer patients. See, for example, Fitzgibbons et al, Arch. Pathol. Lab. Med. 124:966-78, 2000. Tumors that are hormone receptor positive are more likely to respond to hormone therapy and also typically grow less aggressively, thereby resulting in a better prognosis for patients with ER+/PR+ tumors. In a further example, overexpression of human epidermal growth factor receptor 2 (HER-2/neu), a transmembrane tyrosine kinase receptor protein, has been correlated with poor breast cancer prognosis (see, e.g., Ross et al, The Oncologist 8:307-25, 2003), and Her-2 expression levels in breast tumors are used to predict response to the anti-Her-2 monoclonal antibody therapeutic trastuzumab (Herceptin®, Genentech, South San Francisco, Calif.).

In another aspect of the invention, the diseased entity exhibits one or more predisposing factors for malignancy that may be treated by administration of a pharmaceutical composition including the compound. Such predisposing factors include but are not limited to chromosomal translocations associated with a malignancy such as the Philadelphia chromosome for chronic myelogenous leukemia and t (14; 18) for follicular lymphoma; an incidence of polyposis or Gardner's syndrome that are indicative of colon cancer; benign monoclonal gammopathy which is indicative of multiple myeloma, kinship with persons who have had or currently have a cancer or precancerous disease, exposure to carcinogens, or any other predisposing factor that indicates in increased incidence of cancer now known or yet to be disclosed.

The invention further encompasses methods of treating cancer that comprise combination therapies that comprise the administration of a pharmaceutical composition including the disclosed compound and another treatment modality. Such treatment modalities include but are not limited to, radiotherapy, chemotherapy, surgery, immunotherapy, cancer vaccines, radioimmunotherapy, treatment with pharmaceutical compositions other than those which include the disclosed compound, or any other method that effectively treats cancer in combination with the disclosed compound now known or yet to be disclosed. Combination therapies may act synergistically. That is, the combination of the two therapies is more effective than either therapy administered alone. This results in a situation in which lower dosages of both treatment modality may be used effectively. This in turn reduces the toxicity and side effects, if any, associated with the administration either modality without a reduction in efficacy.

In another aspect of the invention, the pharmaceutical composition including the disclosed compound is administered in combination with a therapeutically effective amount of radiotherapy. The radiotherapy may be administered concurrently with, prior to, or following the administration of the pharmaceutical composition including the compound. The radiotherapy may act additively or synergistically with the pharmaceutical composition including the compound. This particular aspect of the invention would be most effective in cancers known to be responsive to radiotherapy. Cancers known to be responsive to radiotherapy include, but are not limited to, Non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophogeal cancer, rectal cancer, small-cell lung cancer, non-small cell lung cancer, brain tumors, other CNS neoplasms, or any other such tumor now known or yet to be disclosed.

Non-limiting examples of pharmaceutical compositions that may be used in combination with the disclosed compound include nucleic acid binding compositions such as cis-diamminedichloro platinum (II) (cisplatin), doxorubicin, 5-fluorouracil, taxol, and topoisomerase inhibitors such as etoposide, teniposide, irinotecan and topotecan. Still other pharmaceutical compositions include antiemetic compositions such as metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron.

Still other examples of pharmaceutical compositions that may be used in combination with the pharmaceutical composition including the disclosed compound are hematopoietic colony stimulating factors. Examples of hematopoietic colony stimulating factors include, but are not limited to, filgrastim, sargramostim, molgramostim and epoietin alfa. Alternatively, the pharmaceutical composition including the disclosed compound may be used in combination with an anxiolytic agent. Examples of anxiolytic agents include, but are not limited to, buspirone, and benzodiazepines such as diazepam, lorazepam, oxazapam, chlorazepate, clonazepam, chlordiazepoxide and alprazolam.

Pharmaceutical compositions that may be used in combination with pharmaceutical compositions that include the disclosed compound may include analgesic agents. Such agents may be opioid or non-opioid analgesic. Non-limiting examples of opioid analgesics inlcude morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, sulindac or any other analgesic now known or yet to be disclosed.

In other aspects of the invention, pharmaceutical compositions including the disclosed compound may be used in combination with a method that involves treatment of cancer ex vivo. One example of such a treatment is an autologous stem cell transplant. In this method, a diseased entity's autologous hematopoietic stem cells are harvested and purged of all cancer cells. A therapeutic amount of a pharmaceutical composition including the disclosed compound may then be administered to the patient prior to restoring the entity's bone marrow by addition of either the patient's own or donor stem cells.

Cancers that may be treated by pharmaceutical compositions including the disclosed compound either alone or in combination with another treatment modality include solid tumors such as fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangio-blastoma, acoustic neuroma, oligodendroglioma, meningioma, skin cancer, melanoma, neuroblastoma, and retinoblastoma.

Additional cancers that may be treated by pharmaceutical compositions including the disclosed compound include blood borne cancers such as acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present disclosure is further illustrated by the following examples that should not be construed as limiting.

EXAMPLES

Compounds

N-hydroxy-2-(2-(4-methoxyphenyl)butanamido)thiazole-5-carboxamide (#1) (M+1: 336)

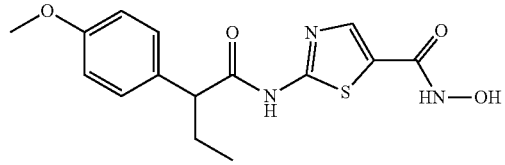

(S)—N-hydroxy-2-(2-(4-methoxyphenyl)butanamido)thiazole-5-carboxamide (#1a)

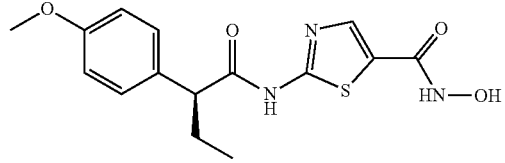 [SMILES: CC[C@H](C(=O)Nc1ncc(C(=O)NO)s1)c1ccc(OC)cc1]

(R)—N-hydroxy-2-(2-(4-methoxyphenyl)butanamido)thiazole-5-carboxamide (#1b)

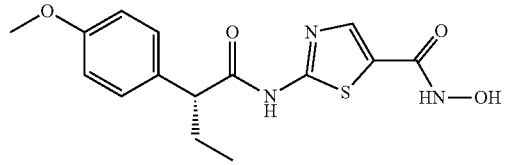 [SMILES: CC[C@@H](C(=O)Nc1ncc(C(=O)NO)s1)c1ccc(OC)cc1]

Synthesis of N-hydroxy-2-(2-(4-methoxyphenyl)butanamido)thiazole-5-carboxamide (#1)

Synthesis of compound #1 follows the following general scheme (FIG. 1). An amide formation reaction between carboxylic acid of formula II and amino thiazole of formula III mediated by N,N,N',N'-Tetramethyl-O-(7-azabenzotriazol-1-yl)uronium hexafluorophosphate (HATU) and diisopropylethylamine (DIEA) in N,N-dimethylformaldehyde (DMF). The coupling product of formula IV is treated with hydroxylamine and sodium hydroxide in tetrahydrofuran and methyl alcohol solution yields the corresponding hydroxamic acid of formula V. Chiral resolution of V provided optically active enantiomer Va. Further chemical transformations such as esterification and sulfonation afforded VI.

(S)—N-hydroxy-2-(2-(4-methoxyphenyl)butanamido)thiazole-5-carboxamide (#1a) and (R)—N-hydroxy-2-(2-(4-methoxyphenyl)butanamido)thiazole-5-carboxamide (#1b)

Step 1. To a solution of 2-(4-methoxyphenyl)butanoic acid (135 mg, 0.70 mmol) and ethyl 2-aminothiazole-5-carboxylate (100 mg, 0.58 mmol) in DMF were added DIEA (112 mg, 0.87 mmol) and HATU (264 mg, 0.70 mmol). The reaction was stirred at room temperature for 4 hrs and partitioned between ethyl acetate and water. The organic layer was dried and concentrated. The residue was purified by biotage column chromatography to afford ethyl 2-(2-(4-methoxyphenyl)butanamido)thiazole-5-carboxylate (163 mg).

Step 2. To a solution of methyl 2-(2-(4-methoxyphenyl)butanamido)thiazole-5-carboxylate (112 mg, 0.322 mmol) in a mixture of tetrahydrofuran/methanol (4:1) was added 2.8 mL of hydroxylamine (50% in water) followed by sodium hydroxide solution (1 N, 1.0 mL). The mixture was stirred at room temperature overnight and concentrated. The residue was acidified with 1 N HCl and purified by C18 biotage column chromatography to afford compound (±)-N-hydroxy-2-(2-(4-methoxyphenyl)butanamido)thiazole-5-carboxamide (71 mg). MS (calculated for M+1: 349; found 349)

Figure 3:
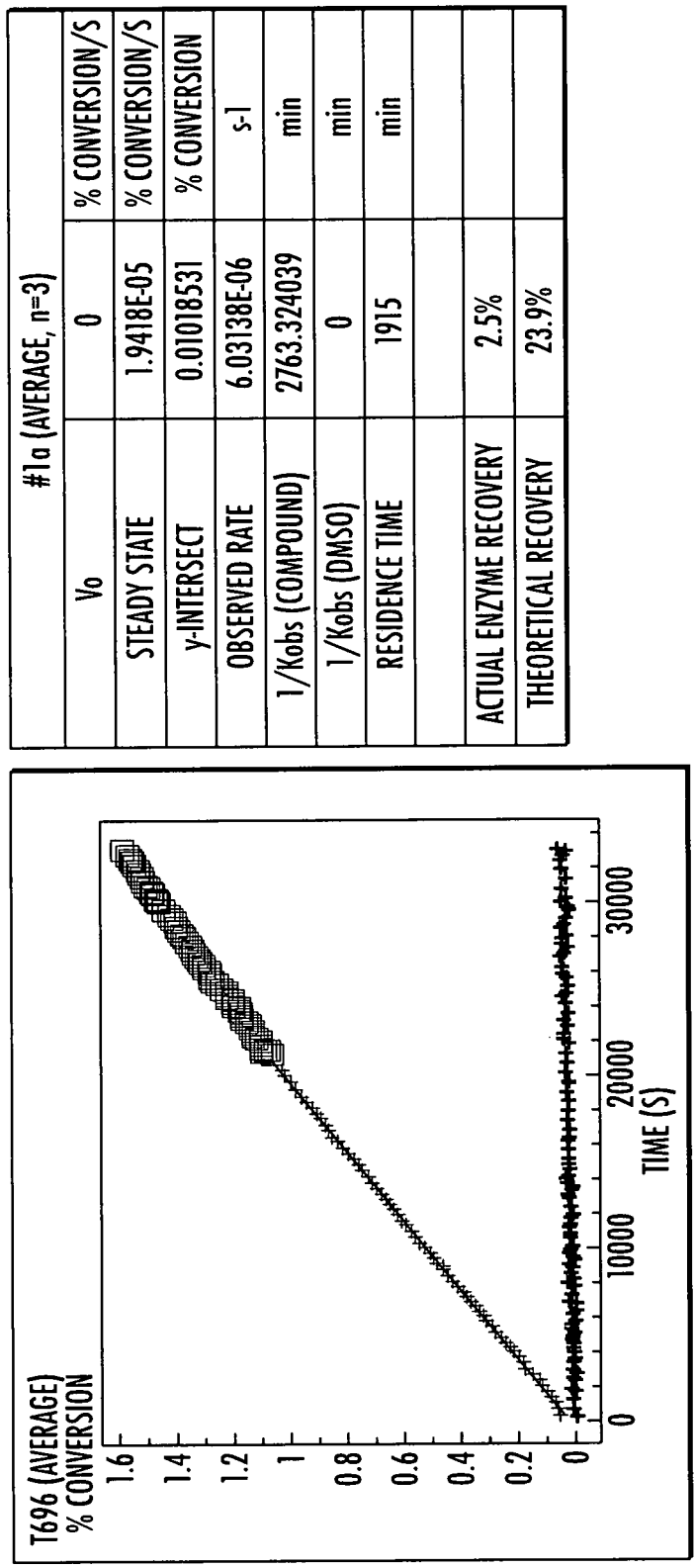
FIG. 3 illustrates the $K_{off}$ kinetics for #1a against HDAC6 enzyme.

Step 3. The racemic mixture from step 2 was resolved by CHIRALPAK® ID-3 to provide two enantiomers, Compound #1a (retention time=1.49 min) and Compound #1b (retention time=4.33) (FIG. 3). The column chromatography conditions were:

Co-Solvent: MEOH:DCM=1:1(0.2% IPA)

Column: CHIRAL PAK ID-3 4.6*250 mm 5um

Injection Volume: 3

Co-Solvent %: 50%

Column Temperature: 36.6 C

Sample Well: P1:3A

Total Flow: 4

Back Pressure: 100

Pressure Drop: 68

Synthesis of (S)—N-hydroxy-2-(2-(4-methoxyphenyl)butanamido)thiazole-5-carboxamide (#1a)

Figure 7:
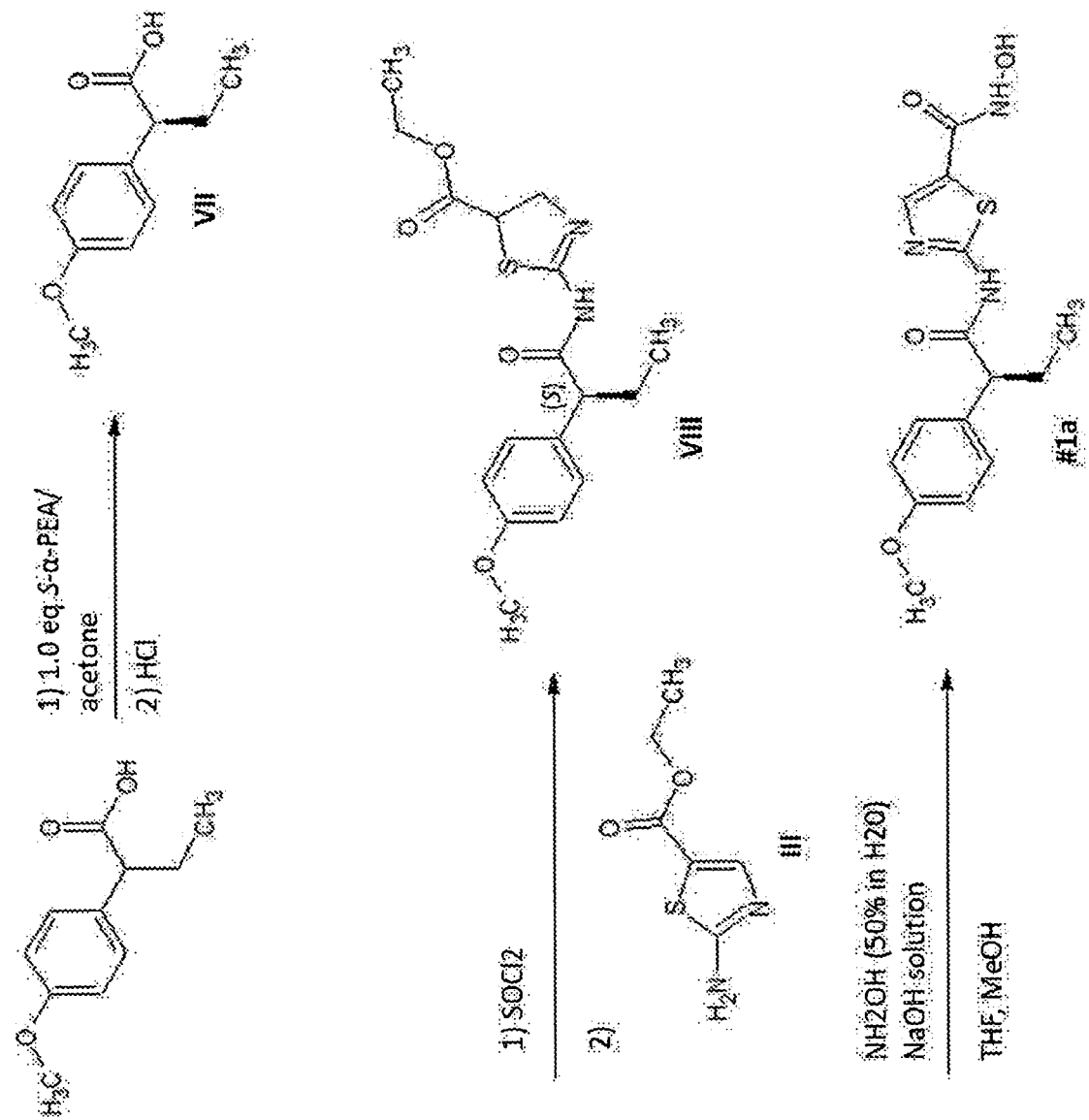
FIG. 7 depicts a synthetic scheme of (S)—N-hydroxy-2-(2-(4-methoxyphenyl)butanamido)thiazole-5-carboxamide (i.e., #1a).

Synthesis of compound #1a follows the scheme shown in FIG. 7

Step 1

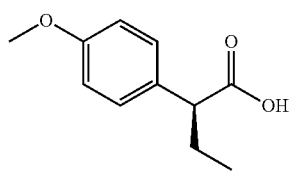

VII

(2S)-2-(4-methoxyphenyl)butanoic acid

S-α-phenethylamine (S-α-PEA) (49.6 g, 1.0 eq.) was dissolved in 400 mL of acetone under $N_2$. To this was added a solution of 2-(4-methoxyphenyl)butanoic acid (80.0 g, 1.0 eq.) in acetone (400 mL) dropwise. The solution was heated to 50-55° C. and stirred for 2 h and cooled to room temperature. The precipitate was filtered, washed with acetone and dissolved in water (1600 mL) and 2 N HCl (60 mL). The solution was extracted with ethyl acetate (3×80 mL). The combined organic phase was washed with water (2×80 mL) and concentrated to give 23.2 g of (2S)-2-(4-methoxyphenyl)butanoic acid (Compound VII) (98.60% LC purity, 98.2% ee).

Step 2

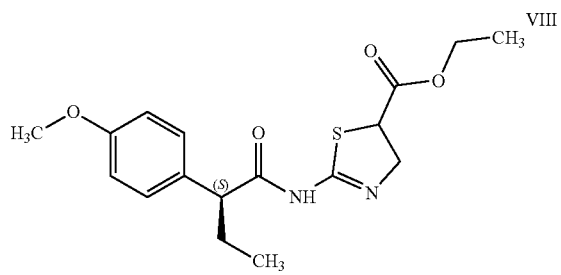

ethyl 2-{[(2S)-2-(4-methoxyphenyl)butanoyl]amino}-1,3-thiazole-5-carboxylate To a solution of Compound VII (22.0 g, 1.0 eq.) in dichloromethane (220 mL) under $N_2$ was added $SOCl_2$ (40.4 g, 3.0 eq.) dropwise at 0° C. The reaction was stirred for 3 h at 5-15° C. and concentrated. The residue was dissolved in THY (330 mL), concentrated to remove the residual $SOCl_2$ and dissolved in THF (330 mL). This acid chloride solution was added to a solution of ethyl 2-amino-1,3-thiazole-5-carboxylate (Compound III) (21.46 g, 1.1 eq.) and triethylamine (25.38 g, 2.0 eq.) in THF dropwise at 0° C. The reaction was warmed to room temperature, stirred overnight and the reaction quenched with water (440 mL) at room temperature. The mixture was extracted with methyl t-butyl ether (460 mL). The organic layer was washed with 1 N HCl (230 mL), 0.5 N $NaHCO_3$ (230 ml) and 5% NaCl (115 mL) and concentrated. The residue was mixed with n-Heptane (230 mL), stirred for 0.5 h at 40-50° C. and then cooled to room temperature. The precipitate was filtered, washed with acetone/n-heptane (1:10, 46 mL). The filter cake was collected, dried bellow 45° C. under vacuum until to give ethyl 2-{[(2S)-2-(4-methoxyphenyl)butanoyl]amino}-1,3-thiazole-5-carboxylate (Compound VIII) (35.8 g).

Step 3

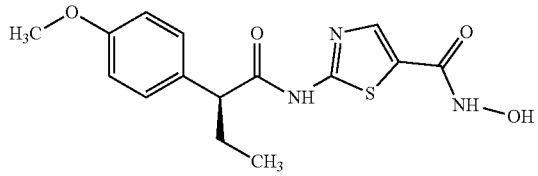

(S)—N-hydroxy-2-(2-(4-methoxyphenyl)butana-
mido)thiazole-5-carboxamide

To a solution of Compound VIII (35.8 g, 1.0 eq.) in THF (720 mL) and MeOH (180 mL) was added 50% $NH_2OH$ (50% in water, 900 mL) To this was added 1 N NaOH (330 mL) dropwise. The reaction was stirred at 15-25° C. overnight and quenched with conc. HCl until the pH was about 6. The mixture was extracted with ethyl acetate (2×720 mL). The combined organic phase was washed with 5% brine (360 mL), concentrated. To the residue was added dichloromethane (540 mL), and the mixture was stirred at room temperature for 1 h. The solid was filtered and washed with DCM (100 mL) and the cake was collected, dried bellow 45° C. under vacuum to give (S)—N-hydroxy-2-(2-(4-methoxyphenyl)butanamido)thiazole-5-carboxamide (#1a) (27.9 g).

Inhibition of HDAC Enzymes by #1a and #1b

Compounds were tested in a 12-point concentration-response format against 11 HDAC enzymes as outlined in Table 2A. Test compounds were diluted in 100% DMSO using 3-fold dilution steps. The final compound concentration in the assay ranged from 100 µM to 0.565 nM or as requested. Compounds were tested in a single well for each dilution, and the final concentration of DMSO in all assays was kept at 1%. Reference compounds were tested in an identical manner. The results are presented in Table 2B.

Effects of #1, #1a, and #1b on Cell Viability

Cell viability in the presence of varying concentrations of the above listed compounds at different time points was used to assess cytotoxicity and the effect of the compounds on cell proliferation. $IC_{50}$ (or percent activity) data for the disclosed compounds in cell lines are summarized in Table 3.

Cell Viability Assay

Cell viability was measured by the CellTiter-Glo® cell viability assay from Promega (Madison, Wis.). The CellTiter-Glo® Luminescent Cell Viability Assay is a homogeneous method to determine the number of viable cells in culture based on quantitation of the ATP present, which signals the presence of metabolically active cells. Following treatment, CellTiter-Glo® is added to treatment wells and incubated at 37° C. luminescence values were measured at using a Molecular Devices Spectramax microplate reader Single Agent Studies Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours. Treatment with the test agents or standard agents began on Day 1 and continued for 72 hours. At the 72-hour timepoint, treatment containing media was removed. Viable cell numbers are quantified by the CellTiter-Glo® cell viability assay as described above. Results from these studies were used to calculate an $IC_{50}$ value (concentration of drug that inhibits cell growth by 50 percent of control) for each compound.

Data Collection

For single agent and combination studies, data from each experiment was collected and expressed as % Cell Growth using the following calculation:

% Cell Growth=$(f_{test}/f_{vehicle}) \times 100$

Where test is the fluorescence of the tested sample, and $f_{vehicle}$ is the fluorescence of the vehicle in which the drug is dissolved. Dose response graphs and $IC_{50}$ values were generated using Prism 6 software (GraphPad) using the following equation:

$Y = (\text{Top-Bottom})/(1+10^{((logIC_{50}-X)\cdot HillSlope)})$

Where X is the logarithm of concentration and Y is the response. Y starts at the Bottom and goes to Top with a sigmoid shape.

TABLE 2A

| | Assay | Enzyme Preparation Vendor.CatNo.LotNo | [Enzyme], nM | Substrate Conc (µM) | Incubation Time (hr) |
|---|---|---|---|---|---|
| 1 | HDAC1 | BPS.50051.17I115-1 | 5 | 1 | 17 |
| 2 | HDAC2 | BPS.50002.160701 | 7.5 | 1 | 17 |
| 3 | HDAC3 | BPS.50003.110404 | 0.5 | 1 | 3 |
| 4 | HDAC4 | in-house.42606 | 1 | 1 | 1.5 |
| 5 | HDAC5 | BPS.50045.130620 | 0.25 | 1 | 3 |
| 6 | HDAC6 | in-house.71114 | 60 | 1 | 5 |
| 7 | HDAC7 | in-house.459-26 | 0.2 | 1 | 3 |
| 8 | HDAC8 | BPS.50008.131120-1 | 1.25 | 1 | 3 |
| 9 | HDAC9 | BPS.50009.91007 | 0.5 | 1 | 3 |
| 10 | HDAC10 | in-house.47336 | 450 | 1 | 17 |
| 11 | HDAC11 | in-house.06052014 | 10 | 2 | 17 |

TABLE 2B

| HDAC | 1 | 2 | 3 | 4 | 5 | 6 | 7 | 8 | 9 | 10 | 11 |
|---|---|---|---|---|---|---|---|---|---|---|---|
| 1a ($IC_{50}$ nM) | 1.0 | 5.3 | <0.56 | 138 | 73.5 | 0.71 | 34.5 | 133 | 187 | 2.0 | 5780 |
| 1b ($IC_{50}$ nM) | 7.8 | 36.5 | 2.6 | 160 | 100 | 1.1 | 118 | 416 | 210 | 14.6 | 4220 |
| Fold (1b/1a) | 7.8 | 6.9 | 4.6 | 1.2 | 1.4 | 1.5 | 3.4 | 3.1 | 1.1 | 7.3 | 0.73 |

TABLE 3

| Cell Line | Tissue Type | #1 IC$_{50}$ (μM) | #1a IC$_{50}$ (μM) | #1b IC$_{50}$ (μM) | #1/#1a | #1b/#1a |
|---|---|---|---|---|---|---|
| OVARIAN | | | | | | |
| BIN-67 | Human Small Cell Carcinoma of the Ovary | 0.068 | 0.051 | 0.45 | 1.33 | 8.82 |
| COV434 | Human Ovarian Granulosa | 0.047 | 0.035 | 0.339 | 1.34 | 9.69 |
| SCCOHT-1 | Human Small Cell Carcinoma of the Ovary | 0.341 | 0.293 | 0.185 | 1.16 | 0.63 |
| A2780 | Human Ovarian | 0.048 | 0.032 | 0.219 | 1.5 | 6.84 |
| A2780cp | Platinum res-Human Ovarian | 0.117 | 0.062 | 0.378 | 1.89 | 6.1 |
| OVCAR-3 | Human Ovarian Carcinoma | 0.065 | 0.039 | 0.244 | 1.67 | 6.26 |
| OVCAR-8 | Human Ovarian Carcinoma | 0.036 | 0.021 | 0.113 | 1.71 | 5.38 |
| SKOV-3 | Human Ovarian Carcinoma | 0.113 | 0.063 | 0.509 | 1.79 | 8.08 |
| IGROV-1 | Human Ovarian Adenocarcinoma | 0.078 | 0.054 | 0.49 | 1.44 | 9.07 |
| OAW28 | ovarian cystadenocarcinoma | 0.288 | 0.085 | 0.562 | 3.39 | 6.61 |
| BREAST | | | | | | |
| MDA-MB-468 | TNBC | 0.068 | 0.06 | 0.55 | 1.13 | 9.17 |
| MDA-MB-231 | TNBC | 0.113 | 0.062 | 0.646 | 1.82 | 10.42 |
| HCC70 | TNBC | 0.1 | 0.052 | 0.341 | 1.92 | 6.56 |
| 4T1 | Murine Breast Tumor | 0.036 | 0.023 | 0.185 | 1.57 | 8.04 |
| MCF7 | ER + BCC | 0.039 | 0.021 | 0.158 | 1.86 | 7.52 |
| HCC1806 | acantholytic squamous cell carcinoma | 0.179 | 0.071 | 0.465 | 2.52 | 6.55 |
| MDA-MB-157 | Medullary Carcinoma | 0.169 | 0.089 | 0.558 | 1.9 | 6.27 |
| BT-20 | Carcinoma | 0.236 | 0.093 | 0.759 | 2.54 | 8.16 |
| SUM149PT | IBC | 0.191 | 0.074 | 0.612 | 2.58 | 8.27 |
| BT474 | Ductal Carcinoma | 1 | 0.145 | 3.02 | 6.9 | 20.83 |
| HEMATOPIETIC | | | | | | |
| DOHH-2 | Lymphoma | 0.016 | 0.017 | 0.135 | 0.94 | 7.94 |
| MV411 | AML | 0.007 | 0.006 | 0.023 | 1.17 | 3.83 |
| L1210 | Murine Leukemia | 0.059 | 0.038 | 0.324 | 1.55 | 8.53 |
| L363 | MM | 0.044 | 0.021 | 0.17 | 2.1 | 8.1 |
| J1M-1 | MM | 0.047 | 0.026 | 0.219 | 1.81 | 8.42 |
| KMS-34 | MM | 0.015 | 0.013 | 0.067 | 1.15 | 5.15 |
| RPMI-8226 | MM | 0.031 | 0.014 | 0.129 | 2.21 | 9.21 |
| MOLP-8 | MM | 0.013 | 0.013 | 0.032 | 1 | 2.46 |
| KMM-1 | MM | 0.02 | 0.019 | 0.105 | 1.05 | 5.53 |
| OCI-Ly3 | DLBCL | 0.065 | 0.035 | 0.17 | 1.86 | 4.86 |
| CCRF-CEM | ALL | 0.028 | 0.014 | 0.113 | 2 | 8.07 |
| MOLM-13 | AML | 0.062 | 0.028 | 0.209 | 2.21 | 7.46 |
| K562 | CML | 0.145 | 0.078 | 0.398 | 1.86 | 5.1 |
| THP-1 | AML | 0.065 | 0.032 | 0.196 | 2.03 | 6.13 |
| KG-1 | AML | 0.022 | 0.012 | 0.148 | 1.83 | 12.33 |
| MM1.S | MM | 0.033 | 0.012 | 0.071 | 2.75 | 5.92 |
| Nalm-6 | ALL | 0.026 | 0.011 | 0.091 | 2.36 | 8.27 |
| Raji | Burkitt's | 0.105 | 0.036 | 0.282 | 2.92 | 7.83 |
| LUNG | | | | | | |
| A549 | NSCLC | 0.076 | 0.052 | 0.398 | 1.46 | 7.65 |
| H23 | NSCLC | 0.076 | 0.047 | 0.424 | 1.62 | 9.02 |
| H460 | NSCLC | 0.079 | 0.05 | 0.363 | 1.58 | 7.26 |
| H1650 | NSCLC | 0.363 | 0.174 | 1.202 | 2.09 | 6.91 |
| NCI-H226 | Mesothelioma | 0.479 | 0.2 | 1.687 | 2.4 | 8.44 |
| H522 | NSCLC | 0.178 | 0.115 | 0.977 | 1.55 | 8.5 |
| A427 | Carcinoma | 0.309 | 0.186 | 1.445 | 1.66 | 7.77 |
| H1975 | NSCLC | 0.114 | 0.04 | 0.398 | 2.85 | 9.95 |
| NCI-H820 | NSCLC | 0.085 | 0.054 | 0.398 | 1.57 | 7.37 |
| MSTO-211H | Mesothelioma | 0.128 | 0.052 | 0.352 | 2.46 | 6.77 |
| H358 | NSCLC | 0.158 | 0.069 | 0.558 | 2.29 | 8.09 |
| NCI-H209 | Carcinoma | 0.11 | 0.016 | 0.251 | 6.88 | 15.69 |
| NCI-H1963 | Carcinoma | 0.196 | 0.026 | 0.407 | 7.54 | 15.65 |
| LK-2 | Carcinoma | 0.196 | 0.04 | 0.398 | 4.9 | 9.95 |
| PANCREAS | | | | | | |
| BxPC-3 | Pancreatic | 0.251 | 0.174 | 1.096 | 1.44 | 6.3 |
| MiaPaCa | Pancreatic | 0.051 | 0.035 | 0.289 | 1.46 | 8.26 |
| ASPC-1 | Pancreatic | 0.158 | 0.112 | 0.813 | 1.41 | 7.26 |
| Panc-1 | Pancreatic | 0.631 | 0.302 | 2.673 | 2.09 | 8.85 |
| YAPC | Pancreatic | 0.437 | 0.215 | 1.963 | 2.03 | 9.13 |
| Capan-2 | Pancreatic | 0.363 | 0.136 | 0.97 | 2.67 | 7.13 |

TABLE 3-continued

| Cell Line | Tissue Type | #1 IC$_{50}$ (µM) | #1a IC$_{50}$ (µM) | #1b IC$_{50}$ (µM) | #1/#1a | #1b/#1a |
|---|---|---|---|---|---|---|
| RENAL | | | | | | |
| G401 | Rhabdoid Tumor | 0.091 | 0.05 | 0.407 | 1.82 | 8.14 |
| G402 | Renal leiomyoblastoma | 0.102 | 0.065 | 0.501 | 1.57 | 7.71 |
| A498 | RCC-VHL mut | 0.063 | 0.047 | 0.352 | 1.34 | 7.49 |
| SN12CCP | RCC | 0.126 | 0.055 | 0.41 | 2.29 | 7.45 |
| ACHN | RCC | 0.229 | 0.078 | 0.736 | 2.94 | 9.44 |
| RXF-393 | RCC | 0.398 | 0.113 | 0.884 | 3.52 | 7.82 |
| LIVER | | | | | | |
| Huh-7-luc | HCC | 0.185 | 0.068 | 0.493 | 2.72 | 7.25 |
| HepG2 | HCC | 0.215 | 0.076 | 0.631 | 2.83 | 8.3 |
| SK-Hep-1 | HCC | 0.374 | 0.149 | 1 | 2.51 | 6.71 |
| ENDOMETRIAL | | | | | | |
| Ishikawa | Endometrial | 0.048 | 0.028 | 0.191 | 1.71 | 6.82 |
| KLE | Endometrial | 0.215 | 0.106 | 0.851 | 2.03 | 8.03 |
| MFE296 | Endometrial | 0.052 | 0.035 | 0.204 | 1.49 | 5.83 |
| AN3CA | Endometrial | 0.066 | 0.047 | 0.229 | 1.4 | 4.87 |
| Hec-1A | Endometrial | 0.056 | 0.037 | 0.309 | 1.51 | 8.35 |
| SKUT-1 | Uterine | 0.229 | 0.215 | 1.259 | 1.07 | 5.86 |
| COLON | | | | | | |
| RKO | CRC | 0.267 | 0.145 | 1.358 | 1.84 | 9.37 |
| HT-29 | CRC | 0.136 | 0.043 | 0.41 | 3.16 | 9.53 |
| GASTRIC | | | | | | |
| SNU-1 | Carcinoma | 0.509 | t0.132 | 1.403 | 3.86 | 10.63 |
| N87 | Carcinoma | 0.12 | 0.018 | 0.331 | 6.67 | 18.39 |
| MURINE COLON | | | | | | |
| CT26 | Colon | 1.318 | 0.465 | 3.214 | 2.83 | 6.91 |
| MC38 | Colon | 0.128 | 0.058 | 0.493 | 2.21 | 8.5 |
| CERVICAL-SQUAMOUS CELL | | | | | | |
| SiHa | | 0.311 | 0.307 | 2.735 | 1.01 | 8.91 |
| MELANOMA | | | | | | |
| MeWo | LN Met | 0.158 | 0.083 | 0.612 | 1.9 | 7.37 |
| A375 | Malignant Melanoma | 0.269 | 0.032 | 0.651 | 8.41 | 20.34 |
| Hs695T | LN Met | 0.372 | 0.052 | 0.97 | 7.15 | 18.65 |
| Hs852T | Melanoma | 0.49 | 0.054 | 1.24 | 9.07 | 22.96 |
| RHABDOMYOSARCOMA | | | | | | |
| A204 | Muscle | 0.033 | 0.054 | 0.17 | 0.61 | 3.15 |
| MURINE BRAIN | | | | | | |
| GL261 | Murine Glioma | 0.372 | 0.132 | 1.202 | 2.82 | 9.11 |
| RETINOBLASTOMA | | | | | | |
| Y79 | Retina | 0.363 | 0.087 | 0.631 | 4.17 | 7.25 |
| H&N SQUAMOUS CELL | | | | | | |
| Cal-27 | Tongue | 0.215 | 0.045 | 0.465 | 4.78 | 10.33 |
| FaDu | Pharynx | 0.01 | 0.04 | 0.331 | 0.25 | 8.28 |
| PROSTATE | | | | | | |
| H660 | LN Met | 0.158 | 0.028 | 0.423 | 5.64 | 15.11 |

Pharmacokinetics

Figure 2:
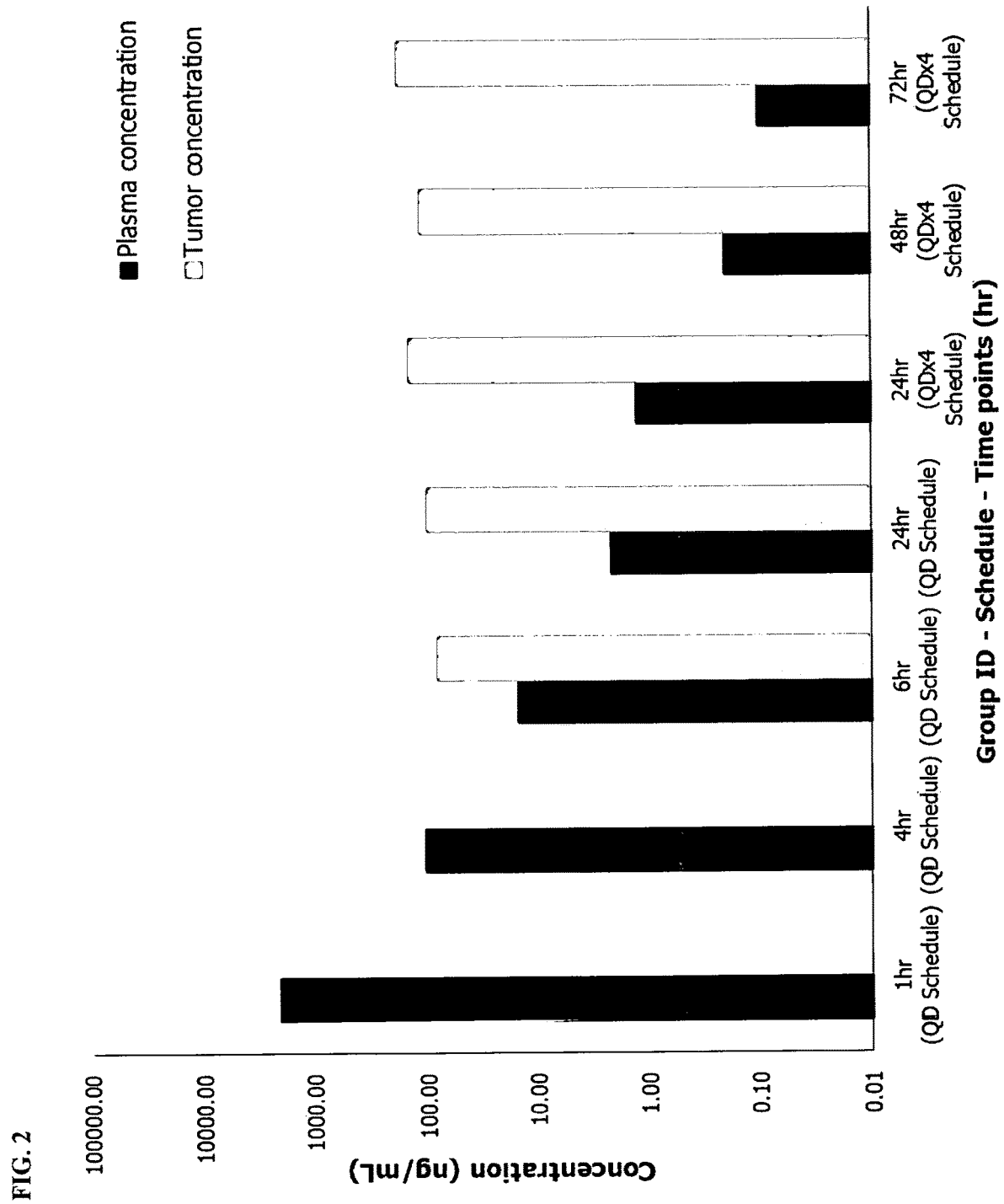

Pharmacokinetics studies of #1, #1a, and #1b in mice are shown in Tables 4 and 5. #1a demonstrates significantly increased Vz/F (Apparent volume of distribution during terminal phase after oral administration) compared to #1 or #1b. Volume of distribution is one of the most important pharmacokinetic properties of a drug candidate and for an anticancer drug can result in increased drug distribution to the tumor. FIG. 2 illustrates that #1a does have preferential and significant tumor uptake and retention.

TABLE 4

| | PO-5 mg/kg | | |
|---|---|---|---|
| PK parameters | #1 | #1a | #1b |
| R-sq | 0.97 | 0.90 | 0.98 |
| Half life (hr) | 5.44 | 5.53 | 3.60 |
| Tmax (hr) | 0.50 | 0.50 | 1.00 |
| Cmax (ng/mL) | 30.79 | 28.74 | 20.85 |

TABLE 4-continued

| | PO-5 mg/kg | | |
|---|---|---|---|
| PK parameters | #1 | #1a | #1b |
| AUC$_{0-last}$ | | | |
| (hr*ng/mL) | 163.00 | 72.85 | 90.44 |
| AUC$_{0-inf}$ | | | |
| (hr*ng/mL) | 172.49 | 74.29 | 91.38 |
| AUC % Extrap | 5.51 | 1.93 | 1.02 |
| Vz/Fobs (L/kg) | 227.54 | 536.76 | 283.83 |
| Cl/Fobs | | | |
| (L/hr/kg) | 28.99 | 67.30 | 54.72 |
| % F | 14.27 | 13.94 | 16.21 |

TABLE 5

Pharmacokinetic study of #1a in mice

| PK parameters | 5% Ethanol 5% Cremophor 90% Saline SC-5 mg/kg | 10% Ethanol 90% Labrasol PO-5 mg/kg | 5% Ethanol 5% Cremophor 90% Saline IV-1 mg/kg |
|---|---|---|---|
| R-sq | 0.99 | 0.90 | 0.84 |
| Half life (hr) | 1.22 | 5.53 | 0.93 |
| Tmax (hr) | 0.25 | 0.50 | 0.25 |
| Cmax (ng/mL) | 251.70 | 28.74 | 130.82 |
| AUC $_{0-last}$ (hr*ng/mL) | 343.92 | 72.85 | 106.35 |
| AUC $_{0-inf}$ (hr*ng/mL) | 346.85 | 74.29 | 106.56 |
| AUC % Extrap | 0.85 | 1.93 | 0.20 |
| Vz/Fobs (L/kg) | 25.34 | 536.76 | 5.07 |
| Cl/Fobs (L/hr/kg) | 14.42 | 67.30 | 9.38 |
| % F | 65.10 | 13.94 | N/A |

Determination of $K_{off}$ Kinetics Against HDAC6 Protein

Figure 4:
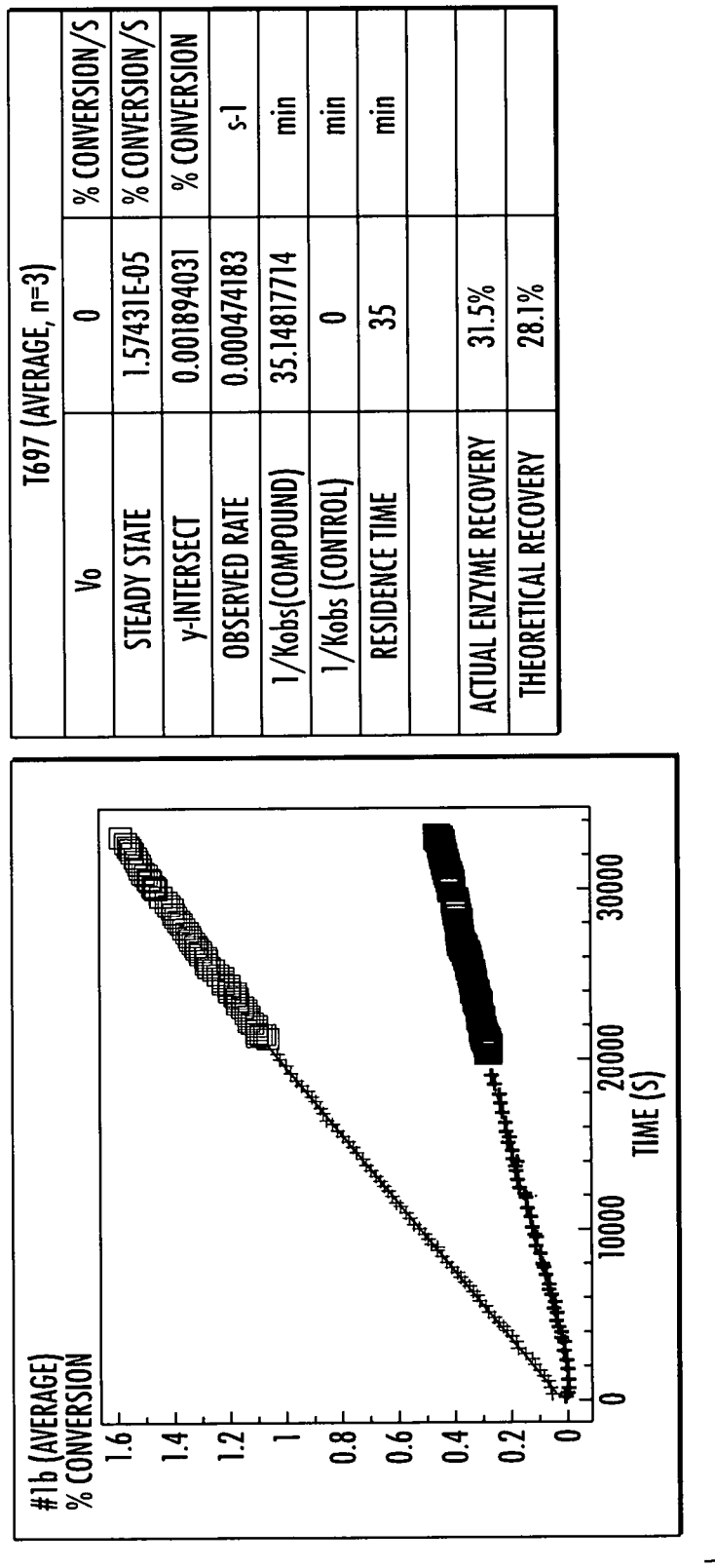
FIG. 4 illustrates the $K_{off}$ kinetics for #1b against HDAC6 enzyme

The disassociation rate for #1a (FIG. 3) or #1b (FIG. 4) was determined by pre-incubating 100 nM HDAC6 protein with 0.120 μM compound #1a, #1b, or DMSO for 3 hr. After pre-incubation, the compound-enzyme complex was diluted (200×) into an assay buffer with substrate peptide. Progress curves for ~8 hrs were observed using Labchip3000 instrument. Progress curve after pre-incubation with compound (blue) was fit with following equation: $((A+(Vs*x))+(((Vo-Vs)*(1-exp(((-1)*Kobs)*t)))/Kobs))$, to determine observed rate of dissociation. Residence time was determined as $Ln(2)/Kobs$.

The results demonstrate surprising and unexpected improvements in $K_{off}$ and residence time for #1a compared to #1b. Compound #1a appears to be a very tightly bound inhibitor of HDAC6. The finding was confirmed by auxiliary dialysis study demonstrating only 5% #1a recovery after 24 hours of dialysis. The residence time for binding of #1a to HDAC6 was 1915 minutes compared to only 35 minutes for compound #1b, a 55-fold increase in residence time for #1a.

X-Ray Crystallography of #1a

Single colorless plate-shaped crystals of (#1a) were recrystallized from a mixture of DCM and methanol by slow evaporation. A suitable crystal (0.47×0.20×0.03) mm³ was selected and mounted on a nylon loop with paratone oil on a Bruker APEX-II CCD diffractometer. The crystal was kept at T=173(2) K during data collection. Using Olex2 (Dolomanov et al., 2009), the structure was solved with the ShelXT (Sheldrick, 2015) structure solution program, using the Intrinsic Phasing solution method. The model was refined with version of XL (Sheldrick, 2008) using Least Squares minimization.

Crystal Data

Figure 5:
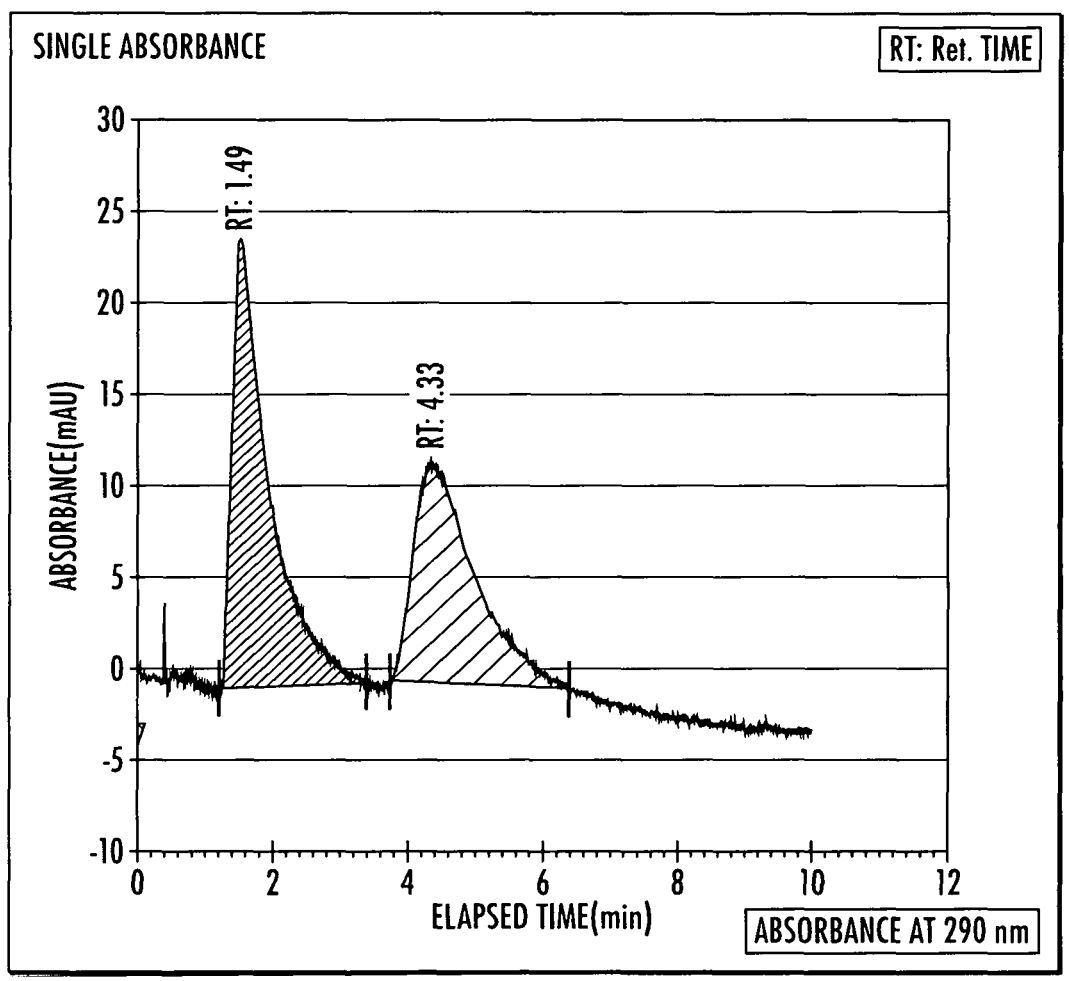
FIG. 5 depicts resolution of #1 by CHIRALPAK® ID-3 to produce two enantiomers, #1a (retention time=1.49 min) and #1b (retention time=4.33).
Figure 6:
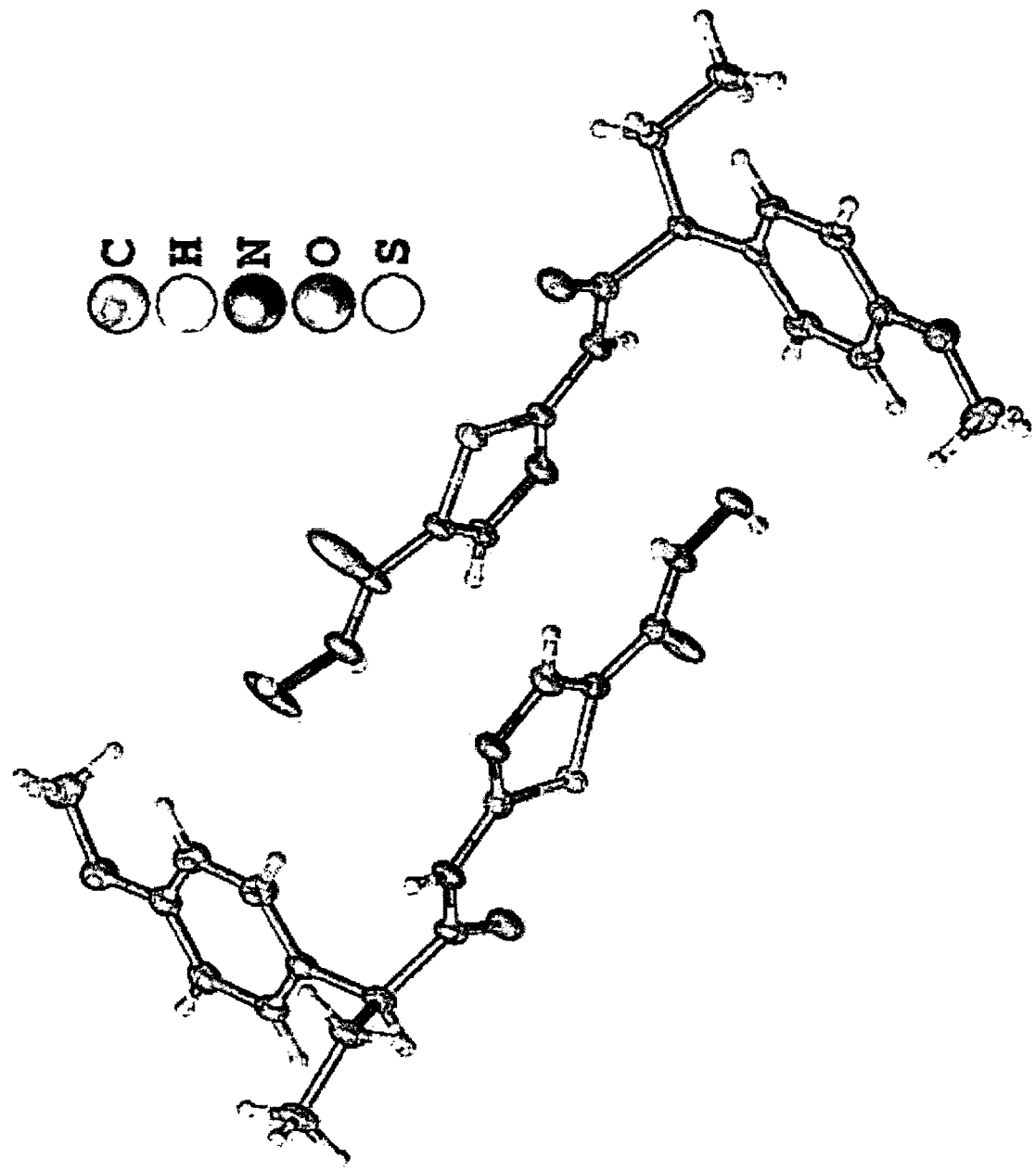

C15H17N3O4S, Mr=335.38, triclinic, P1 (No. 1), a=7.75950(10) Å, b=8.76580(10) Å, c=11.92240(10) Å, α=87.8140(10°), β=73.8220(10°), γ=80.9970(10°), V=769.220(15) Å3, T=173(2) K, Z=2, Z'=2, μ (CuK□)= 2.097, 14374 reflections measured, 4991 unique (Rint=0.0353) which were used in all calculations. The final wR2 was 0.0867 (all data) and R1 was 0.0342 (I>2(I)) (see FIG. 5).

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. COSMO-V1.61—Software for the CCD Detector Systems for Determining Data Collection Parameters, Bruker axs, Madison, Wis. (2000).
2. O. V. Dolomanov and L. J. Bourhis and R. J. Gildea and J. A. K. Howard and H. Puschmann, Olex2: A complete structure solution, refinement and analysis program, J. Appl. Cryst, (2009), 42, 339-341.
3. Sheldrick, G. M., A short history of ShelX, *Acta Cryst.*, (2008), A64, 339-341.
4. Sheldrick, G. M., ShelXT-Integrated space-group and crystal-structure determination, *Acta Cryst.*, (2015), A71, 3-8.
5. Software for the Integration of CCD Detector System Bruker Analytical X-ray Systems, Bruker axs, Madison, Wis. (after 2013).

We claim:

1. A pharmaceutical composition in which the active ingredient consists of:
   (S)-N-hydroxy-2-(2-(4-methoxyphenyl)butanamido)thiazole-5-carboxamide, or a pharmaceutically acceptable salt or solvate thereof.

2. The pharmaceutical composition of claim 1, wherein the (S)-N-hydroxy-2-(2-(4-methoxyphenyl)butanamido)thiazole-5-carboxamide demonstrates significantly increased Vz/F or apparent volume of distribution during terminal phase after oral administration compared to N-hydroxy-2-(2-(4-methoxyphenyl)butanamido)thiazole-5-carboxamide or (R)-N-hydroxy-2-(2-(4-methoxyphenyl)butanamido)thiazole-5-carboxamide indicating preferential and significant tumor uptake and retention.

3. The pharmaceutical composition of claim 1, wherein the pharmaceutically acceptable salt is selected from the group consisting of: aluminum, calcium, magnesium, potassium, sodium, zinc, and combinations thereof.

4. The pharmaceutical composition of claim 1, wherein the pharmaceutical composition comprises a pharmaceutically acceptable carrier selected from the group consisting of: a pharmaceutical polymer carrier, a processing agent, a surfactant, and combinations thereof.

5. The pharmaceutical composition of claim 4, wherein the pharmaceutical polymer carrier is selected from the group consisting of: a cellulosic pharmaceutical polymer, a cross-linked pharmaceutical polymer, a high melt viscosity pharmaceutical polymer, a non-ionic pharmaceutical polymer, a non-ionic, cellulosic pharmaceutical polymer, a non-ionic, water-soluble pharmaceutical polymer, a thermally labile pharmaceutical polymer, a water-soluble pharmaceutical polymer, a water-soluble, cellulosic pharmaceutical polymer, and combinations thereof.

6. The pharmaceutical composition of claim 4, wherein the pharmaceutical polymer carrier is selected from the group consisting of: carbomer, cellulose acetate butyrate, cellulose acetate phthalate, cellulose acetate trimelletate, crospovidone, croscarmellose sodium, dimethylaminoethyl methacrylate-methacrylic acid ester copolymer, ethylacrylate-methylmethacrylate copolymer, ethylcellulose, hydroxyethylcellulose, hydroxypropylcellulose, hydroxypropyl methylcellulose, hydroxypropylmethylcellulose acetate succinate, hydroxypropylmethylcellulose phthalate, poly(butyl methacylate-co-(2-dimethylaminoethyl) methacrylate-co-methyl methacrylate) 1:2:1, polycarbophil, poly(ethylene glycol), poly(ethylene oxide), poly(methacrylate ethylacrylate) (1:1) copolymer, poly(methacrylate methylmethacrylate) (1:1) copolymer, poly(methacrylate methylmethacrylate) (1:2) copolymer, poly(vinyl acetate)-co-poly(vinylpyrrolidone) copolymer, poly(vinyl acetate) phthalate, poly(vinyl alcohol), polyvinyl caprolactam-polyvinyl acetate-polyethylene glycol graft copolymer, poly(vinylpyrrolidone), sodium carboxymethyl-cellulose, and combinations thereof.

7. The pharmaceutical composition of claim 4, wherein the processing agent comprises a plasticizer.

8. The pharmaceutical composition of claim 4, wherein the surfactant is selected from the group consisting of: dioctyl sodium sulphosuccinate, glycerol polyethylene glycol oxystearate-fatty acid glycerol polyglycol esters-polyethylene glycols-glycerol ethoxylate, glycerolpolyethylene glycol ricinoleate-fatty acid esters of polyethylene glycol-polyethylene glycols-ethoxylated glycerol, polyoxyethylene (20) sorbitan monooleate, sodium dodecyl sulfate, sorbitan laurate, vitamin E TPGS, and combinations thereof.

* * * * *